US009622785B2

(12) United States Patent
Sanpera Trigueros et al.

(10) Patent No.: US 9,622,785 B2
(45) Date of Patent: Apr. 18, 2017

(54) SYSTEM AND METHOD FOR A GLOBAL THREE-DIMENSIONAL CORRECTION OF THE CURVATURES OF THE SPINE

(71) Applicants: Ignacio Sanpera Trigueros, Palma Mallorca (ES); Jesús Burgos Flores, Madrid (ES); Eduardo Hevia Sierra, Madrid (ES)

(72) Inventors: Ignacio Sanpera Trigueros, Palma Mallorca (ES); Jesús Burgos Flores, Madrid (ES); Eduardo Hevia Sierra, Madrid (ES)

( * ) Notice: Subject to any disclaimer, the term of this patent is extended or adjusted under 35 U.S.C. 154(b) by 0 days.

(21) Appl. No.: 14/426,102

(22) PCT Filed: Aug. 30, 2013

(86) PCT No.: PCT/EP2013/002615
§ 371 (c)(1),
(2) Date: Mar. 4, 2015

(87) PCT Pub. No.: WO2014/037093
PCT Pub. Date: Mar. 13, 2014

(65) Prior Publication Data
US 2015/0216568 A1  Aug. 6, 2015

Related U.S. Application Data

(60) Provisional application No. 61/696,656, filed on Sep. 4, 2012.

(51) Int. Cl.
*A61B 17/70* (2006.01)
*A61B 17/92* (2006.01)
*A61B 34/10* (2016.01)

(52) U.S. Cl.
CPC ........ *A61B 17/7002* (2013.01); *A61B 17/708* (2013.01); *A61B 17/7038* (2013.01); *A61B 17/7076* (2013.01); *A61B 17/7086* (2013.01); *A61B 17/92* (2013.01); *A61B 34/10* (2016.02); *A61B 2034/105* (2016.02)

(58) Field of Classification Search
CPC .............. A61B 17/7038; A61B 17/708; A61B 17/7076; A61B 17/92; A61B 17/7002; A61B 17/7086
USPC .................................. 606/246–279
See application file for complete search history.

(56) References Cited

U.S. PATENT DOCUMENTS

| | | | |
|---|---|---|---|
| 8,147,524 B2* | 4/2012 | Piza Vallespir .... | A61B 17/7085 606/246 |
| 9,078,709 B2* | 7/2015 | McBride ............ | A61B 17/7076 |
| 9,161,788 B2* | 10/2015 | Daubs ................ | A61B 17/7086 |
| 9,241,742 B2* | 1/2016 | Stad ................... | A61B 17/7074 |
| 2011/0319938 A1* | 12/2011 | Piza Vallespir .... | A61B 17/7076 606/264 |
| 2013/0096624 A1* | 4/2013 | Di Lauro ........... | A61B 17/7011 606/279 |

* cited by examiner

*Primary Examiner* — Pedro Philogene
(74) *Attorney, Agent, or Firm* — Brown & Michaels, PC

(57) ABSTRACT

A three-dimensional correction of the curvatures of the spine, for reducing spinal deformities, such as scoliosis, uses a pair of pedicle screws placed on each of the spinal vertebrae of the spine to be corrected, in combination with alignment elongated members or extenders temporally fixed by a proximate portion and associated with corrective rods engaged with the extenders, running along a transverse plane. Each of the corrective rods provides implant rods.

5 Claims, 34 Drawing Sheets

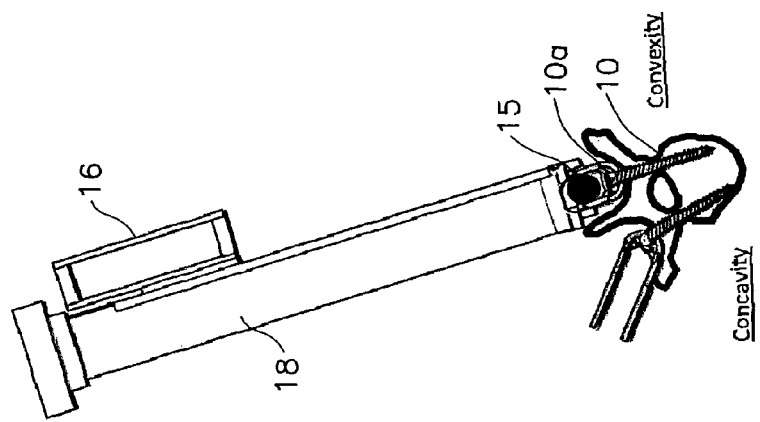
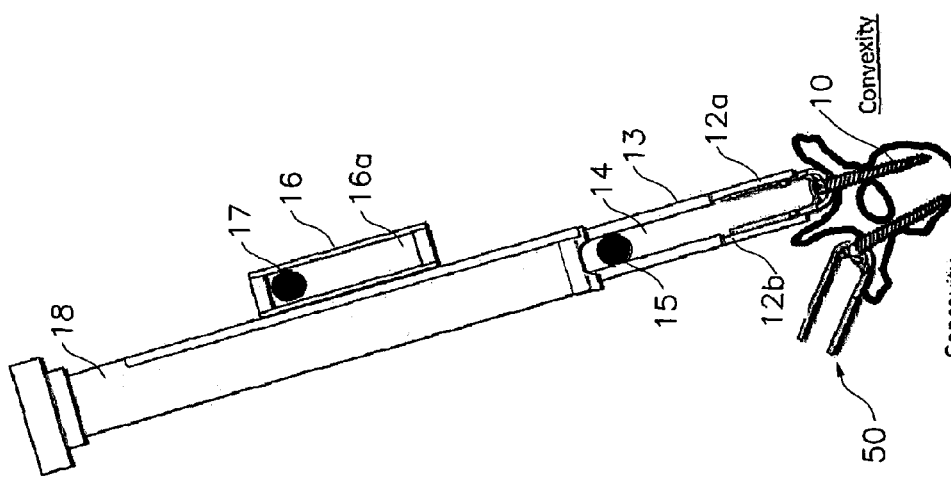

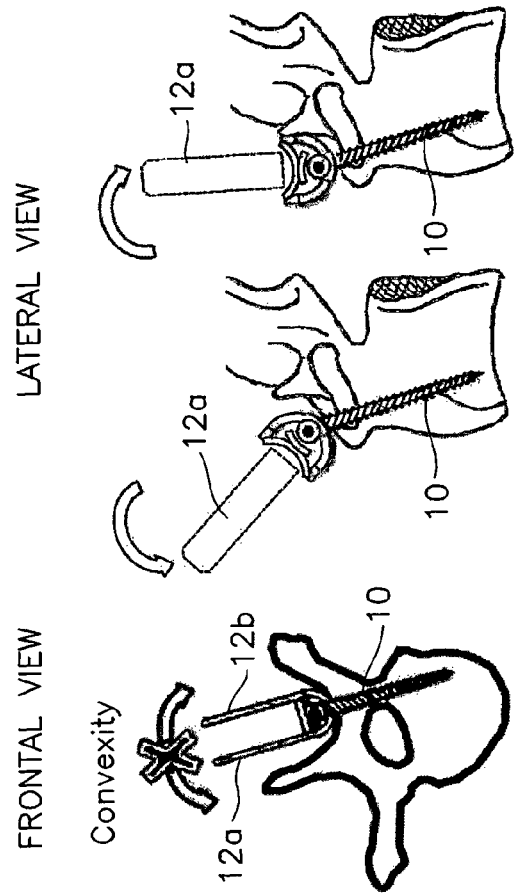
Fig. 11b
Fig. 11a
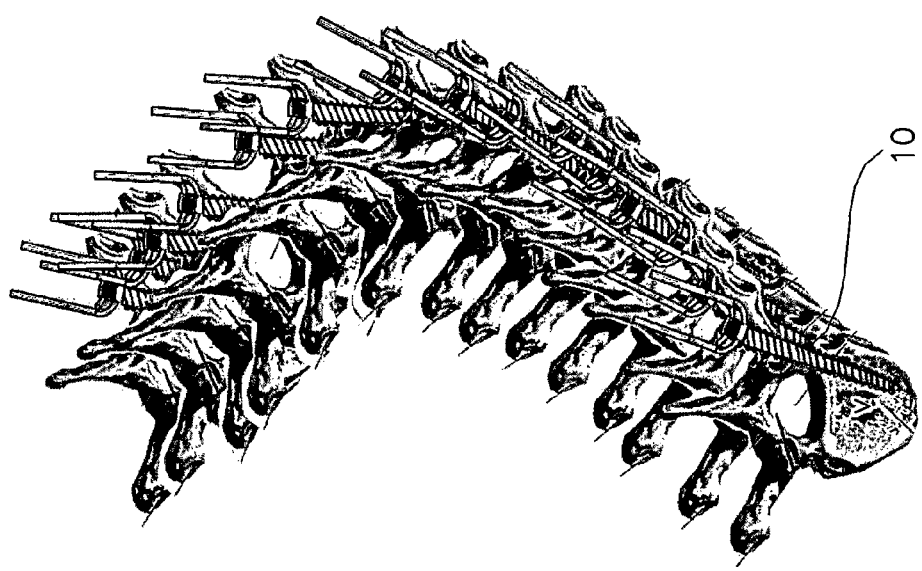
Fig. 11

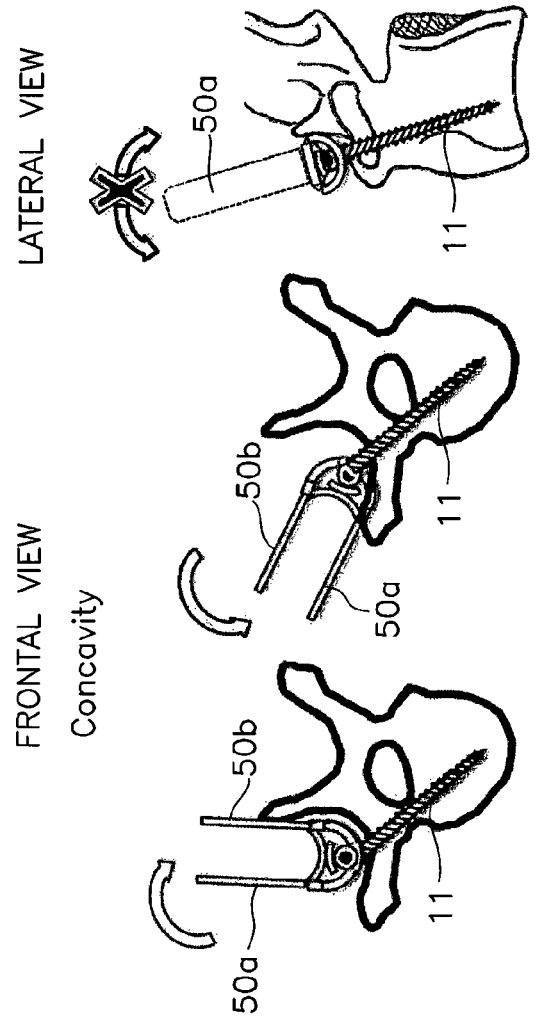
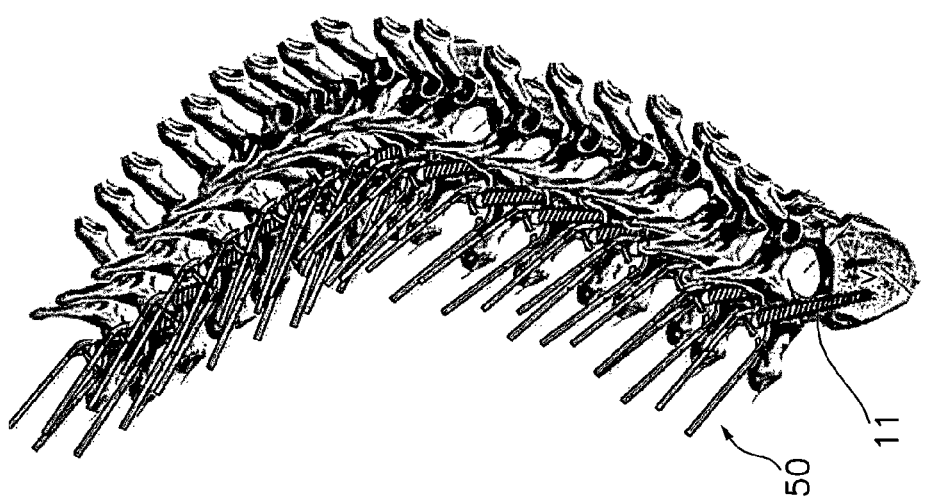

LATERAL VIEW  FRONTAL VIEW
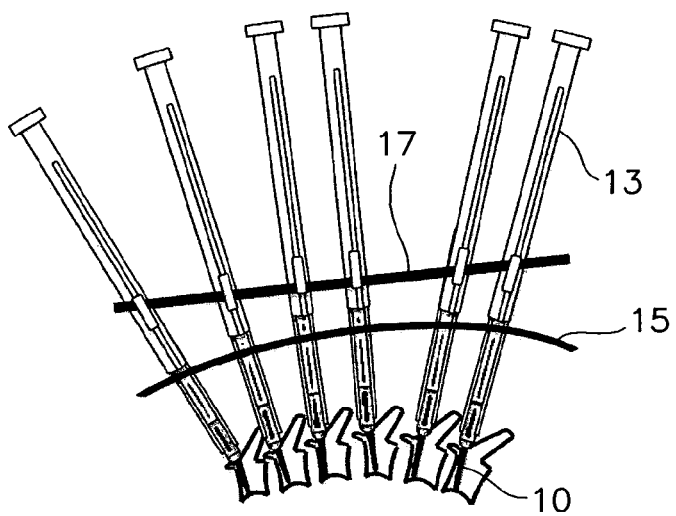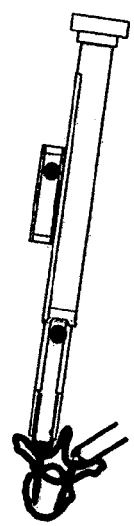
Fig. 18a
LATERAL VIEW  FRONTAL VIEW
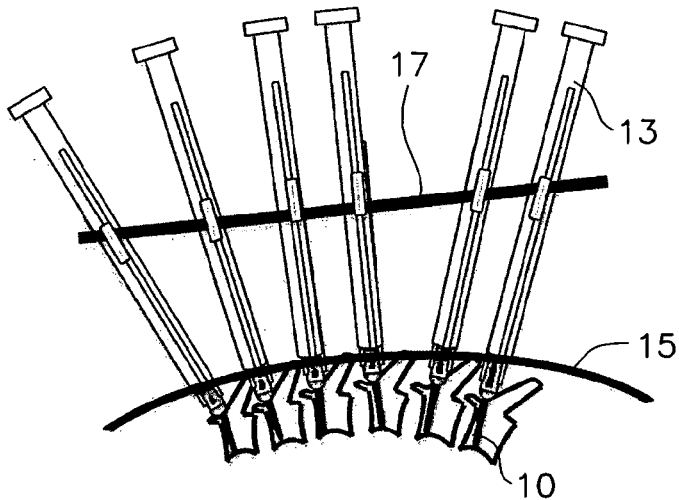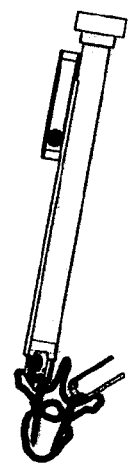
Fig. 18b

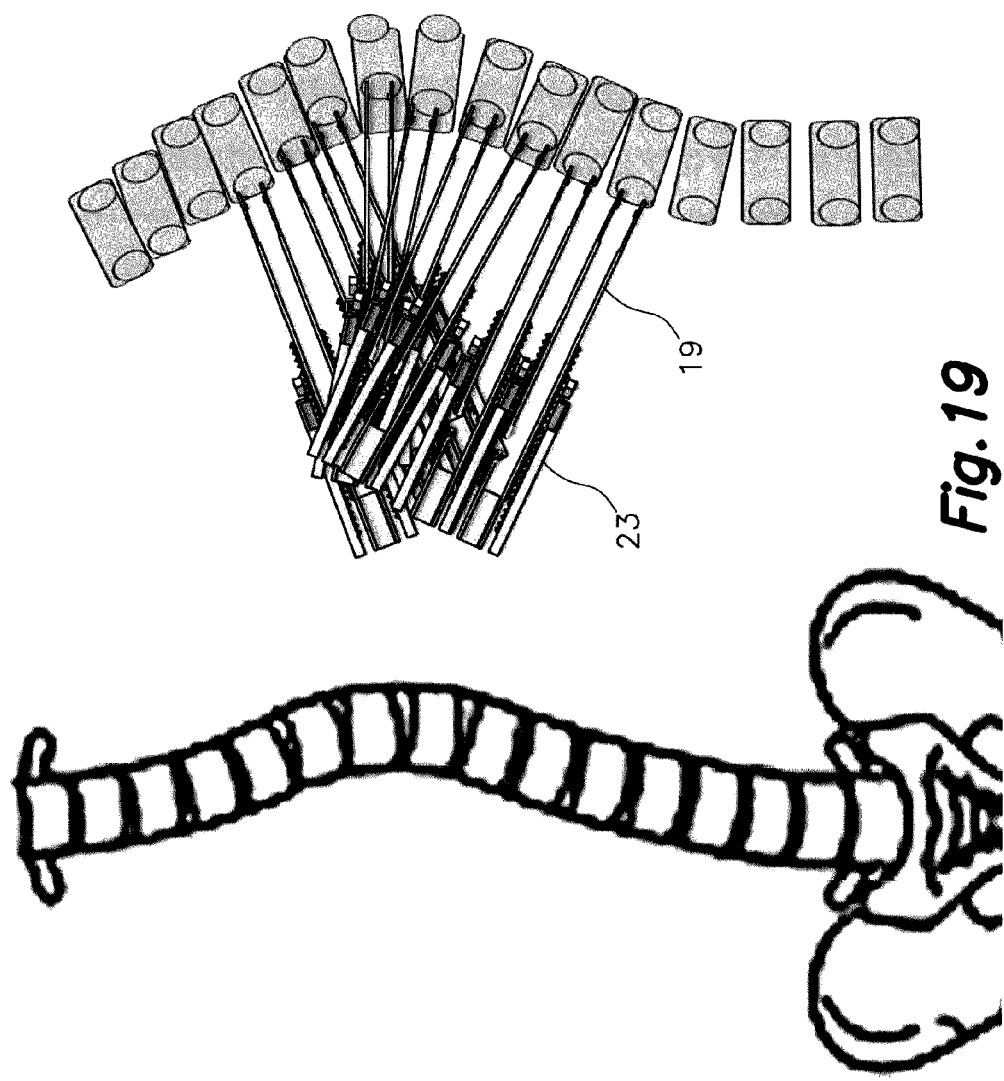

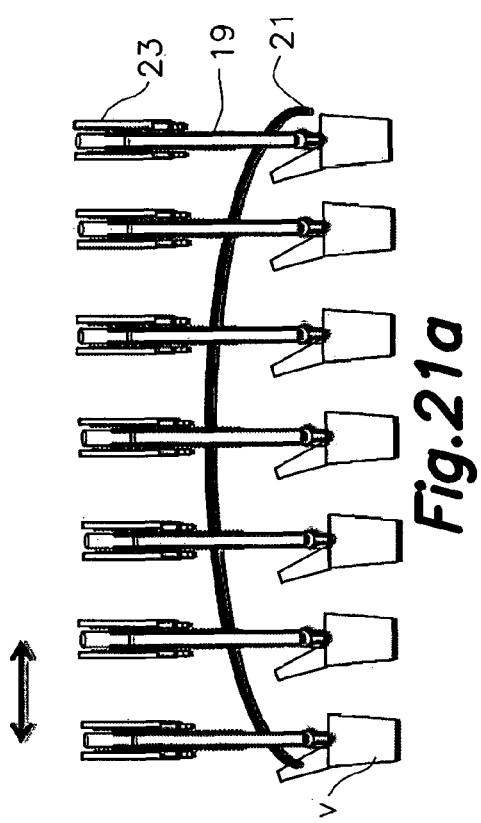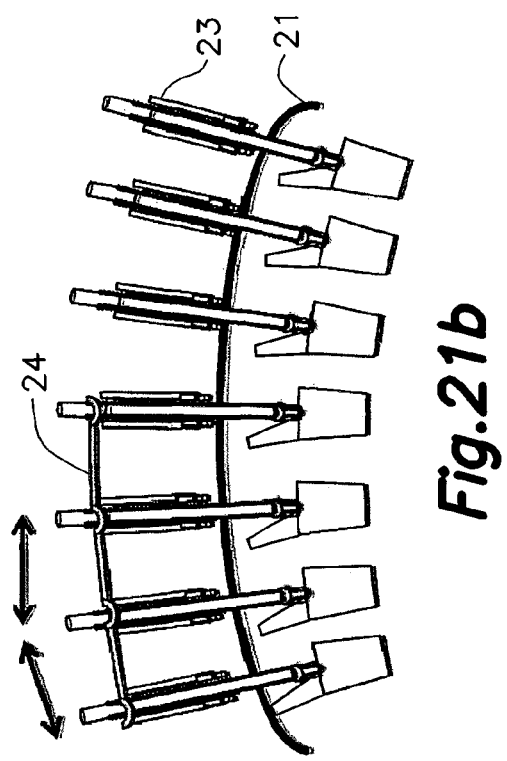

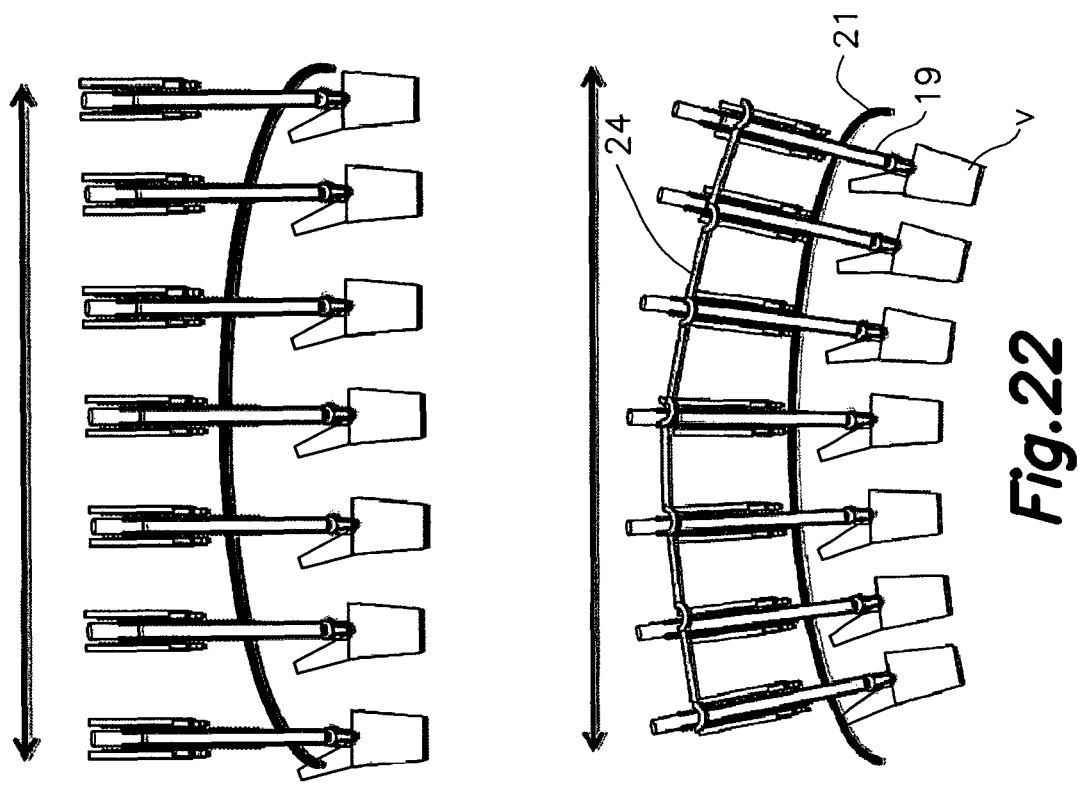

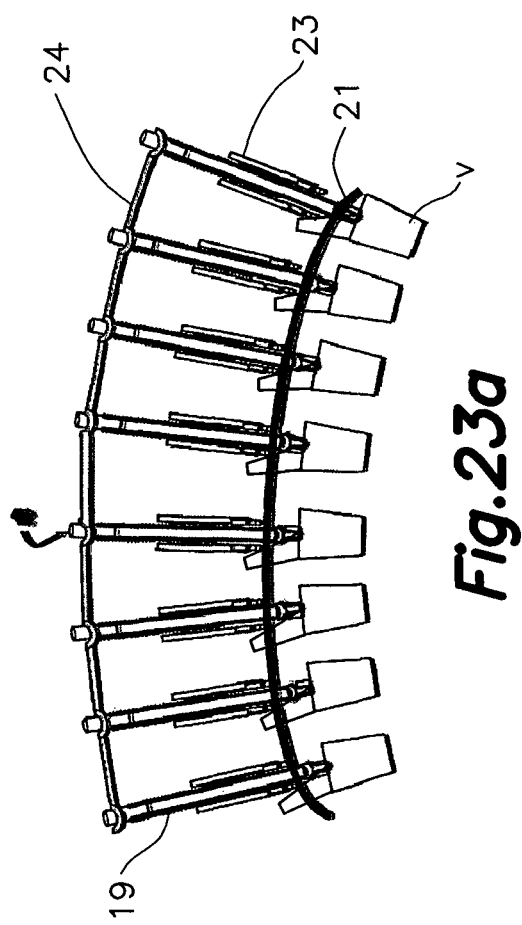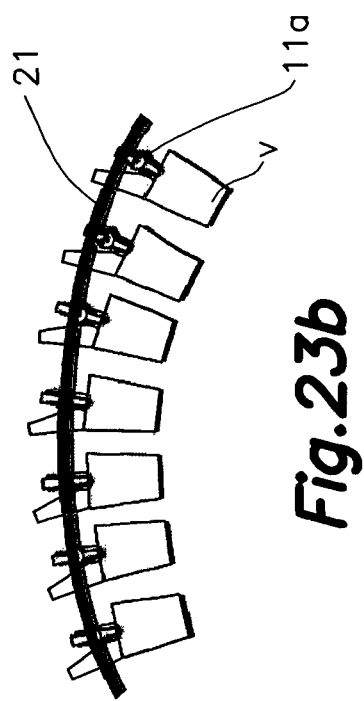

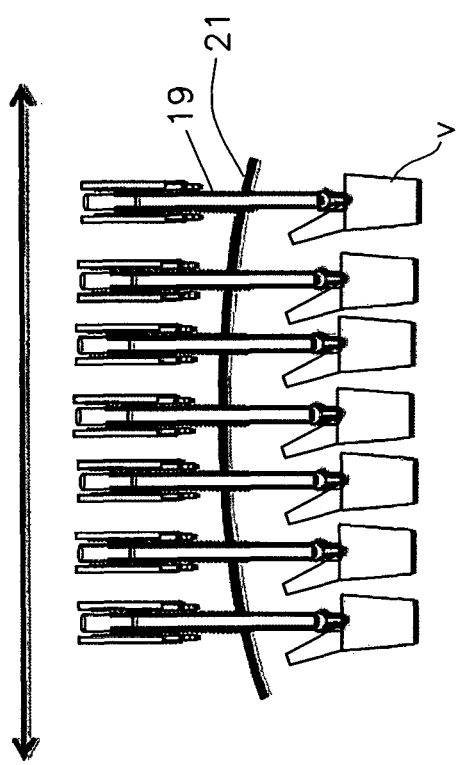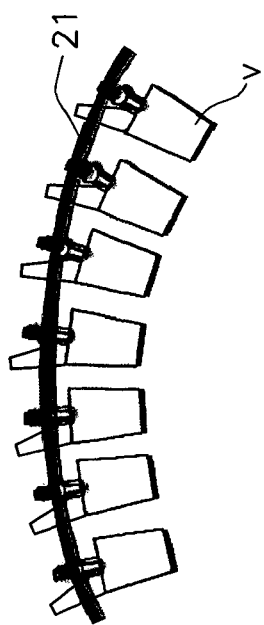
Fig.24a
Fig.24b

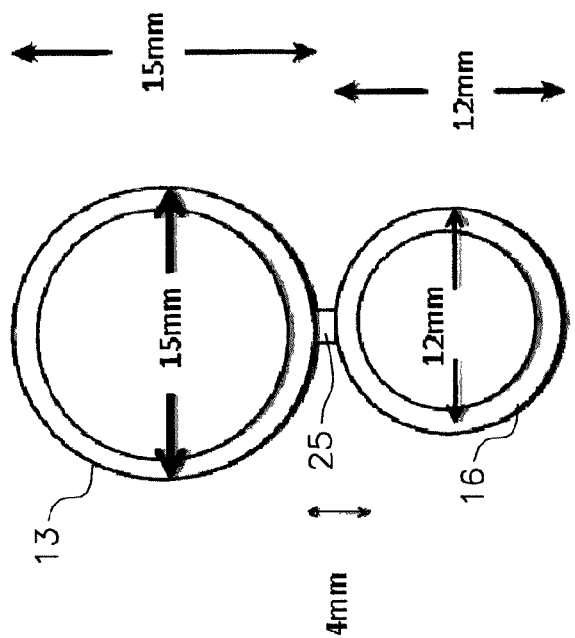
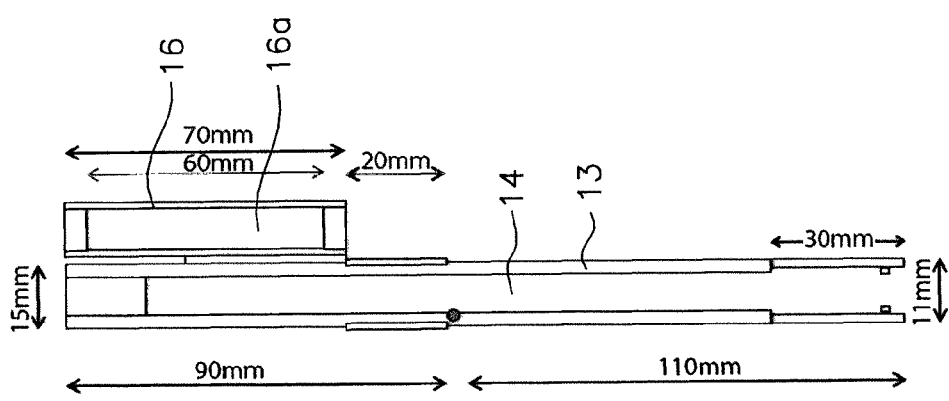

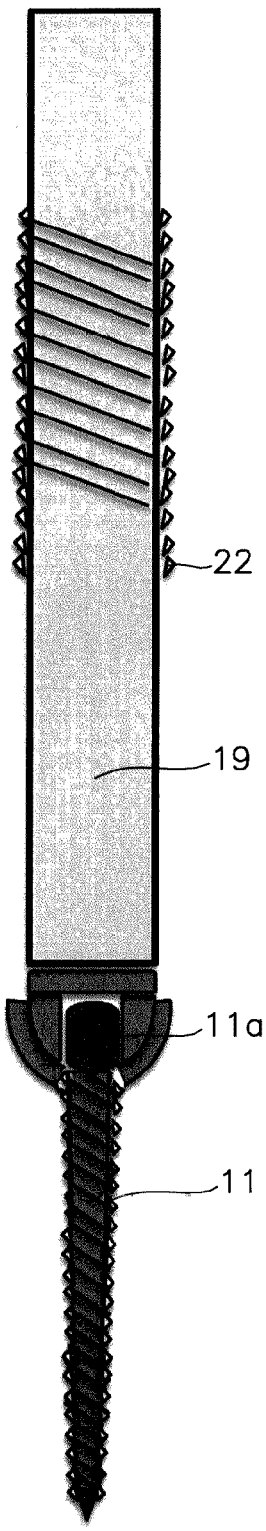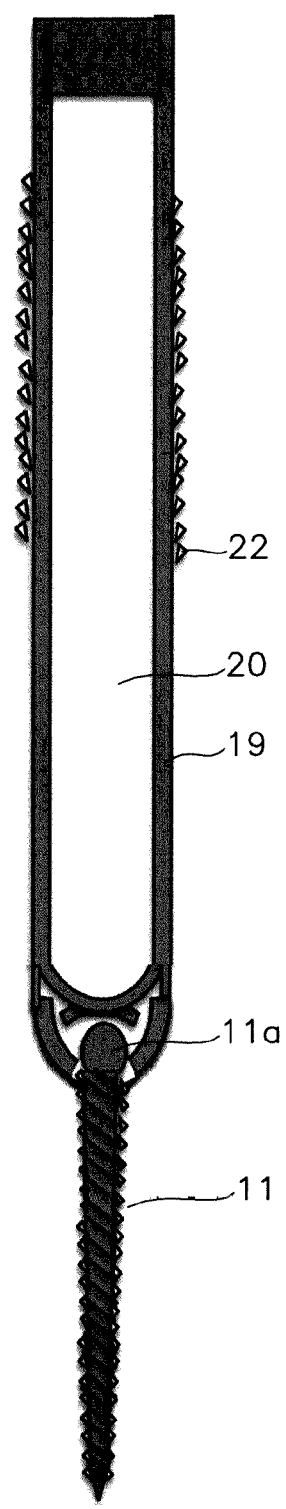
*Fig.44a*   *Fig.44b*

SYSTEM AND METHOD FOR A GLOBAL THREE-DIMENSIONAL CORRECTION OF THE CURVATURES OF THE SPINE

CROSS-REFERENCE TO RELATED APPLICATIONS

This application is the U.S. National Phase under 35. U.S.C. §371 of International Application PCT/EP2013/002615, filed Aug. 30, 2013, which claims priority to U.S. Provisional Application No. 61/696,656, filed Sep. 4, 2012. The disclosures of the above-described applications are hereby incorporated by reference in their entirety.

FIELD OF THE INVENTION

The present invention provides a three-dimensional correction of the curvatures of the spine, for reducing spinal deformities including without limitation scoliosis, by using a pair of pedicle screws placed on each of the spinal vertebrae of the spine to be corrected, in combination with alignment elongated members or extenders temporally fixed by a proximate portion and associated with corrective rods engaged with said extenders, running along a transverse plan, said corrective rods providing implant rods.

The invention also proposes a method for implementing the system.

The spinal column is a complex system of bones and connective tissues that provides support for the human body and protection for the spinal cord and nerves. The adult spine is comprised of 33 vertebral bodies but the sacral and coccix are fused so providing in fact 24 vertebral bodies, which are subdivided into three areas including seven cervical vertebrae, 12 thoracic vertebrae and five lumbar vertebrae. Between each vertebral body is an intervertebral disc that cushions and dampens the various translational and rotational forces exerted on the spinal column.

There are various disorders, diseases and types of injury which the spinal column may experience in a lifetime. The problems may include but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

BACKGROUND OF THE INVENTION

One of the more common solutions to any of the above mentioned conditions involves a surgical procedure known as spinal fusion. A spinal fusion procedure involves fusing two or more vertebral bodies in order to eliminate motion at the intervertebral disc or joint. To achieve this, natural or artificial bone are placed between the vertebrae and frequently a hardware is used to instrument the involved vertebrae to avoid movement and in this way facilitating fusion. In this way damaged or diseased vertebrae are connected to healthy adjacent vertebrae to stabilize the spine while the bone grows and fusion takes place.

The mechanical hardware used to immobilize the spinal column typically involves a series of bone screws and metal rods or plates. When the spine surgery is posteriorly performed, one of the common practices is to place bone screws into the vertebral bodies and then connect a metal rod (usually of titanium or chromium-cobalt alloy or steel) between the bone screws thus creating a rigid structure between adjacent vertebral bodies.

Current systems perform a segmental correction of the curvatures of the spine, immobilizing a group of vertebrae of the spinal deformity center, regardless of the fact that as it is well known scoliosis deformity is a rotating deformity with maximum rotational deformity at the central vertebra of the curve and this deformity decreasing progressively towards the curve ends (periphery), so that the correction required in each vertebrae included in the curve deformity is different and various corrective forces are needed at each level.

Several approaches in the field are following detailed:

A spinal stabilization system suitable for performing spine surgery appears disclosed in EP 2366349, U.S. Pat. No. 7,563,264 and U.S. Pat. No. 7,491,218, where a bone fastener assembly with a collar that allows for angulation of a bone fastener relative to the collar in a conical range of motion is revealed. U.S. Pat. No. 7,914,558 and U.S. Pat. No. 7,691,132 disclose a similar method for inserting a spinal stabilization system in a human spine.

U.S. Pat. No. 8,147,524 refer to a method of reducing a spinal deformity where a pair of bone anchors is attached of each of the vertebrae of the spinal section injured and the pair of bona anchor are interconnected with a bridge member to which correction metal rods as previously referred are attached.

US 2011/0319938 disclose a coplanar deformity correction system involving a bone anchor assembly including a bone anchor, a receiver mounted to the bone anchor, a saddle within the receiver, a spacer within the receiver and an engaging member.

U.S. Pat. No. 8,221,474 reveals a method for assembling a system for correcting alignment of a spinal column of a patient using a des-rotation handle to a transverse bridge between first and second implant holders attached to a vertebra.

FR 2971698 disclose a device for the correction of spine deformations comprising pedicle screws arranged to be connected by a rod bent implantable, rods intended to be engaged through different tubular elements to align corresponding to the correction of said spine, by translation, rotation and rocking of the vertebrae.

U.S. Pat. No. 8,221,426 disclose a spinal alignment system comprising a plurality of pedicle assemblies including pedicle posts and adapter to couple the pedicle posts and a holder to couple to the adapter.

The system of this invention applies the mechanical correction that specifically requires each vertebra.

EP 1774919 refers to a bone anchoring device revealing anchoring elements for a spinal alignment system wherein the movement of the anchoring element before locking is limited to a single plane by a form-fit connection between a head of the anchoring element an a pressure element.

Cited current systems use for the correction of spinal deformities pedicle screws and extenders thereby improving the lever arm to apply corrective forces, but all systems apply the same methodical correction to both sides of the spine, and this despite the fact that convex side and the concave side have opposite deformities. The convexity of scoliosis has an increased posterior perimeter (the lengths between posterior elements is increased) and presents a relative kyphosis deformity, while in the concave side the posterior perimeter is shortened and in addition is lordotic. Therefore, these differing deformities require unlike correctives forces to be applied on both sides, and this approach on which is based this invention has not been applied previously.

According to the inventors also no current system performs a preoperative calculation of the correction to be applied in each patient with scoliosis.

SUMMARY OF THE INVENTION

The system here proposed provides a systematic preoperative calculation of the correction to be applied on each of the sides of the deformed spine. That is, the correction to apply to each level of the spinal deformity can be selected pre-operatively and applied intraoperatively. With this system the correction will be predictable, measurable and calculated preoperatively. This will shorten the operation time and improve surgical outcomes in obvious benefits to the patients.

The system of this invention also uses different pedicle screws in the convex side of the spine of the curve and in the concave side, these terms being used with regard to FIG. 1 of the drawings, for two reasons: to adapt to the requirements of different correcting deformities of one and opposite side and to avoid certain mechanical stresses that may be at risk either side. Therefore the bone anchoring screws provide a movement of the extenders (connected to a head of the screw) in a single plane, allowing for a correction of the convexity, i.e. providing only a cephalic-caudal mobility (allowing movement in the sagittal axis) and a preferential correction on the transverse plane as the corrective forces are applied in the lateral axis following the screws the reduction rod, as is the only degree of freedom available. Besides this type of connection of the head of the screw to the extenders is the most suitable taking into account the expected biomechanical stresses in the convexity making it less likely "sweeping of these screws" with regard to the ones of the concavity. Screws used in the concave side of the spine provide also a movement of the extenders (connected to a head of the screw) in a single plane, providing a lateral-medial mobility (transverse axis) and reducing the spine tangential stresses, following the screw axis and perpendicular to the spine, which are dangerous on this side of the spine, enhancing lordotic deformity correction, which is the priority at this level. In fact The tangential stresses are dangerous in both sides, but the nature of the correction applied, being preferentially sagital on the concave side, increases the intensity of such forces on the concave side. By giving kyphosis (correcting lordosis) we also lengthen the posterior elements distance, and movement in the transverse plane in the convex side added to the sagittal displacement in the concave side necessarily result in a change in the axial plane and hence results in a three-dimensional correction. Once the correction has been achieved, the implanted rod itself locks the possible movement of the screw's head on relation to the pedicle screw to the pedicle screw. That is on tightening the rod to the head, it locks the movement system therefore maintaining the correction achieved. By correcting the transverse plane on the convexity and the sagittal plane on the concavity will necessary result in a modification in the axial plane and therefore will result in a tridimensional correction of the spine.

Screws with a pair of extending elongated flat flanges may be used to facilitate anchoring of a reduction element or rod. This type of screws have been previously used for the correction of scoliosis but never using different uniaxial screws (providing movement of extenders in a single plane) in the concavity and convexity. Other kind of screws with short flat flanges can also be applied.

The system presents two methods and, consequently, two different correction systems within the same instrumentation, one to correct the deformities of the scoliosis produced on the convex side, producing mainly transverse correction and lordosis and another to correct the deformity of the concavity producing mainly kyphosis and completing the derrotation that was not achieved on the convex side Extenders used on each side of the curve are different and their biomechanics action is distinct. The extenders of the convexity are designed to move only in a single sagittal plane and correct mainly in a transversal plane, the correction maneuvers are hipokyphotic and tend to lengthen the posterior perimeter, but do not flatten the spine as the corrective rod is molded with certain kyphosis. As the spine in the convexity was hyperkyphotic and was lengthened (on relation to the concavity), a reduction maneuvers that produces hypokyphosis and shortening, will result mainly in the correction of the vertebral translation and in a partial correction of the vertebral rotation. These extenders are complemented by impact sleeves coaxial to the extenders that push the convexity rod to be implanted by impaction, a gesture intrinsically hypokyphotic, correcting the increased kyphosis (on relation to the concave side) of this side of the deformity and this mechanism of lowering or descending the reduction rod avoid the pull-out forces acting over the screws of this side.

The extenders for the concavity are pivotable in a transverse plane perpendicular to referred sagittal plane, to allow for a correction of the concavity of the deformed spine occurring mainly in a sagittal plane.

Spacers are provided at the distal ends of said extenders used for correcting the concavity and they are designed to maintain kyphosis and at the same time protect or at least decrease against "pull-out" forces on the concave screws. The implant rod is descend or lowered slowly, progressive and softly by sliding by a torque system screwing a ring coaxial to the extenders as later explained in greater detail, delivering corrective forces along all screws. The preferential movement of the screws in a transverse plane also helps to protect against the pull-out forces as the rod is forced down far away from the screw axis. The preferential correction of the transverse plane on the convex side and the sagittal plane in the concave will result in the correction of the existing vertebral rotation The extent length of these kyphosing spacers are preoperatively determined depending on the total curve magnitude, rotation and the amount of kyphosis aimed preoperatively These spacers allow certain telescoping regulation in length during the descend of the rod due to their design of a telescopic structure. Thus, as said separators are preoperatively tailored or quantified they fit the degree of correction required for each level over the concave side.

A basic description of the invention is following presented that will be complemented by a description supported in several drawings.

The invention provides a system for a global three-dimensional correction of the curvatures of the spine, wherein for each of a plurality of vertebrae of a section of the spine to be corrected it comprises:

a first bone anchoring element configured to be anchored into a vertebra;

a second bone anchoring element configured to be anchored into said same vertebra; wherein:

both said first and second bone anchoring elements constitute a pedicle screw and have an axial part for insertion into the vertebra in the form of a threaded shaft having an accessible head;

said head of said first and second bone anchoring elements having pivotally connected thereto a receiving part, to which an alignment elongate member or extender, running along a longitudinal axis is temporally attached by a proximal portion thereof, said receiving part defining a housing;

the extenders attached to said first bone anchoring element include a longitudinal transversal slot allowing insertion therethrough in a plurality of said elongated members of a first corrective rod, said longitudinal slot connecting with said housing and allowing said first corrective rod to be displaced from the top to the bottom of the extender until reaching said housing of said receiving part to become there implanted and reduce the spinal deformity;

the extenders attached to said second bone anchoring element include a longitudinal transversal slot allowing insertion therethrough in a plurality of said elongated members of a second corrective rod, said longitudinal slot connecting with said housing and allowing said second corrective rod to be displaced along the extender until reaching said housing of said receiving part to become there implanted and reduce the spinal deformity;

said receiving part connected to said head of said first bone anchoring elements is pivotable in a single sagittal plane to allow for a correction occurring mainly in a transversal plane of the convexity of the spine by means of the arrangement of said first corrective rod in said housing and said receiving part connected to said head of said second bone anchoring element is pivotable in a transverse plane perpendicular to said sagittal plane, to allow for a correction of the concavity of the deformed spine occurring mainly in a sagittal plane as the bone anchoring member follows said second corrective rod by adopting a suitable angulation, and said elongate members are removed once corrective rods 15, 21 are implanted; once the rod is tightened to the screw head on either side of the spine the pivotable mechanism is locked.

The receiving part comprises a pair of extending elongated or short flat flanges facing each other and defining said housing between them. In an alternative embodiment extenders are obtained as extension of flanges delimiting said receiving part.

According to an embodiment extenders attached to said first bone anchoring element, further includes near its distal end a retaining member including a passage for insertion therethrough of a centering rod extending along a transverse plan engaged with said distal end of said elongate members to temporarily maintain said distal portions in general alignment relative to a first transverse axis prior to insertion of said first corrective rod trough said slot. The centering rod is removed at a later moment once said first corrective rod is implanted into the screw head.

The extenders are tubular alignment members with a transverse longitudinal slot with a portion of said tubular member defining said slot, pivotally articulated so that and end of a lowest part of the tubular member being movable in order to catch a section of said elongated flat flanges of the receiving part to temporally fastening both said end proximal part and elongated flat flanges.

In an embodiment proximal ends of said tubular alignment members have an internal lug and said flat flanges have an opening to receive said lug inserted therein providing said fastening.

In the case of extenders attached to said first bone anchoring elements (for correction of the convexity) a tubular sleeve provided with a longitudinal slit surrounds said extenders and acts as impact member for displacement of said first corrective rod towards their implant position in said housing, adjacent said first bone anchoring head.

On the other hand extenders fastened to said second bone anchoring elements (concavity side) are tubular and have an external part of their surface threaded and an inner threaded ring coaxially coupled to said elongated members in order to push and displace said second corrective rod by being threaded onto said alignment tubular member until reaching a contact with said head of the second bone anchoring element and remaining there as an implanted corrective member.

Moreover telescopically extendable spacers are coupled at the distal ends of said extenders fastened to the second bone anchoring elements (concavity side), cooperating in the alignment of said elongated members during the displacement of said second corrective rod.

As a feature of this invention the mentioned first and second corrective rods are manufactured with a curvature necessary to correct the spine, on the basis of pre-operative tests conducted on radiographies of a patient based on a method where rods are contoured according to a desired correction.

Referred bone anchoring member has an axial part for insertion into the vertebra and said head has two sections which are located opposite to each other and which have spherical outer surface and between said two opposite spherical surfaces of the head comprises two directly facing shaped surfaces and wherein said receiving part has a housing with two opposite spherical concave parts and two opposite shaped parts, so that depending on the position of the head of the anchoring member a pivotal movement in a single plane of the receiving member with regard to said head is permitted, said single plane being selected from a sagittal plane for said first bone anchoring element and from a transversal plane for said second bone anchoring element. The remainder surfaces of the mentioned head are flat therefore preventing movement in other directions.

As per one embodiment of the invention said two directly opposed shaped surfaces of the head of the first and second bone anchoring member are cylindrically-shaped surfaces with the cylinder axis being perpendicular to a longitudinal axis of said axial part of the bone anchoring member and extending through the center of the head and wherein said housing of said receiving part has two opposite cylindrical parts.

As previously indicated telescopically extendable spacers are coupled at the distal ends of said extenders fastened to second bone anchoring elements, cooperating in the alignment of said tubular members during the displacement of the second corrective rod. Therefore threading of said inner threaded ring is provided onto each of the tubular members temporally secured to said second bone anchoring members until fixing said reduction element to the head of said second bone anchoring members, while said second reduction element extending through said tubular members attached to said first bone anchoring members is still not attached.

Thus, in the correction of the concavity, the pull-out traction maneuvers applied onto the pedicle screws when lowering the second corrective rod to be implanted are much lower, by two mechanism, as the pull out forces into the screws are tangential to the spine (following the screw axis), starting the descend from the medial side, away from the pull out forces direction makes the movement safer. Furthermore, the placement of the spacers of top of the extenders produces a divergence of the extenders moving again away form the plane tangential forces that weakens the construct. The spacers are designed to open or close progressively (for this reason they have a telescopically construction) as the corrective rod descends, avoiding creating excessive divergent forces. In this way the rod is lowered until its final position, avoiding therefore these dangerous forces.

The final shape of the rods to be implanted to correct the convexity and concavity is calculated preoperatively using a methodical provided by the inventors that will be further exposed.

The first corrective rod for correcting the convexity of the spine is introduced first (approached to the head of the pedicle screws of the convex side) and, once placed in its final position, lock nuts are placed on the screws loosely except the two proximal screws (to avoid rod rotation). The idea of such action is to allow certain movement of the screws along the first reduction rod (first reduction element), and therefore the vertebrae will be able to rotate about this corrective rod when corrective forces are applied in the concavity side. Otherwise, the correction of the deformities of the concavity (the hipokyphosis and shortening) would become impossible as the convexity rod would act resisting any further movement.

The rod to correct the concavity deformation is molded to allow a correction of the lordosis and the remaining rotation at this level. Because the second reduction rod is molded en hiperkyphosis, the kyphosis of the rod will be bigger in the most rotated part in a way that the bigger the rotation the farther away that will be initially the rod from the screw head, and the bigger the derrotation applied at this level when descending the second reduction rod.

The proposed system with preoperative calculation of the shape of the corrective rods (first and second corrective element) to remain implanted allow for a full or partial correction, predetermined and predictable of scoliosis, that current systems can not achieve. This is the first orderly correction of scoliosis deformity independently considering the convexity and the concavity and applying systems for each level correction thus preoperatively planned results specified by the surgeon can be achieved.

The system of this invention realistically consents performing minimally invasive surgery for scoliosis, allowing correction without molding in situ of the correction rods to be implanted.

The invention also standardizes a method for a global three-dimensional correction of the curvatures of the spine, wherein for each of a plurality of vertebrae of a section of the spine to be corrected comprising:

anchoring to a vertebra of a spine section to be corrected a first and a second anchoring members having an axial part for insertion into the vertebra and a head provided with a receiving part pivotally connected, said receiving part providing a housing;

attaching to said receiving part of said first anchoring member an extender including a longitudinal transversal slot connecting with said housing;

inserting a reduction or centering rod through a passage of a retaining member integral of a distal part of said alignment elongated member said centering rod extending along a transverse plan engaged with said distal end of said elongate members to temporarily maintain said distal portions in general alignment relative to a first transverse axis inserting a first corrective rod trough said longitudinal transversal slot in a plurality of said extenders and descending said first corrective rod from the upper part of the extender, towards the housing of the anchoring element to become there implanted and reduce the spinal deformity;

removal of said centering rod attaching to said receiving part of said second anchoring member an extender including a longitudinal transversal slot connecting with said housing;

inserting a second corrective rod trough said longitudinal transversal slot, in a plurality of said extenders and descending said second corrective rod from the upper part of the extender, towards the housing of the anchoring element to become there implanted and reduce the spinal deformity, and extenders removal once corrective rods are implanted.

wherein receiving part connected to said head of said first bone anchoring elements is pivotable in a single sagittal plane allowing for a correction mainly in a transversal plane of the convexity of the spine by means of the arrangement of said first corrective rod in said housing and said receiving part connected to said head of said second bone anchoring element is pivotable in a single transverse plane perpendicular to said sagittal plane, allowing for a correction of the concavity part of the deformed spine mainly in a sagittal plane as the bone anchoring member follows said second corrective rod. The correction of the translation in the transverse and sagittal plane results in addition to the correction of the spinal rotation deformity

BRIEF DESCRIPTION OF THE DRAWINGS

FIG. 6 illustrate a further step of assembling the elements of the proposed system, showing an alignment elongated member or extender constructed in accordance with the invention, attached to the receiving portion pivotally connected to the head of the pedicle screw for correction of the convexity. In this figure the centering rod inserted in the retaining member of said extender and the first corrective rod (reduction rod to be implanted) placed on the long longitudinal slot are also embodied.

FIG. 7 is equivalent to the previous figure but with a sleeve lowered and with the first corrective rod close to the head of the pedicle screw but still not attached to it and with the centering rod having been removed.

FIG. 11 is a drawing indicating the placement of the pedicle screws and receiving parts intended for correction of the convexity side of the spine curvature.

FIG. 11a is a front section of one pedicle screw of FIG. 11 showing the impediment for a movement in the transverse plane of the receiving part pivotally connected to the head of the pedicle screw.

FIG. 11b illustrates the possibility of movement in a single sagittal plane (craneo-caudal) of the receiving part of the pedicle screw for correcting the convexity.

FIG. 12 is a drawing indicating the placement of the pedicle screws and receiving parts intended for correction of the concavity side of the spine curvature.

FIG. 12a illustrates the possibility of movement in a single medial-lateral plane of the receiving part of the pedicle screw of FIG. 12 for correcting the concavity.

FIG. 12b is a lateral section of one pedicle screw of FIG. 12 showing the impediment for a movement of the receiving part pivotally connected to the head of the pedicle screw in a sagittal plane.

FIGS. 18a and 18b are views equivalent to FIG. 17 showing the placement of the first corrective rod in a first position (FIG. 18a and in a second near final position in FIG. 18b) obtaining a flattening of the kyphosis and important shortening of the extension of the deformed section of the spine.

FIG. 19 is a drawing illustrating over radiography of a patient with spine scoliosis placement of other extenders (having a different structure to be defined below) for correction of convex side of spine.

FIG. 21a illustrate in a lateral view the situation of the extenders with placement of the kyphosis reduction rod at a distance of its final position against the pedicle screws, evidencing the flattening and loss of kyphosis of the vertebrae and FIG. 21b illustrate the situation after placement of some spacers increasing the outside perimeter with the reduction rod still apart from its final position.

FIG. 22 is equivalent to FIG. 21b but with completion of the placement of the spacers at the distal ends of the extenders obtaining an increased kyphosis and lengthening of the outside perimeter FIGS. 23a and 23b illustrate in a lateral view the placement or the second corrective rod (rod pushed down in FIG. 23a) and final position reached in FIG. 23 b fixing said corrective rod to screws and removal of the extenders.

FIGS. 24a and 24 b show in a lateral view comparatively the situation of the vertebrae in the initial phase of placement of the second corrective rod or reduction rod for the concavity (equivalent to FIG. 21a) and the final situation with kyphosis reconstitution and increase of the length of the posterior column.

FIG. 26 is a side view detailing structure of an alignment tubular element or extender used for correction of the convexity.

FIG. 27 is a top plan view of the tubular element of FIG. 26.

FIGS. 36a to 36d illustrate an embodiment of spacers used over distal ends of the tubular extenders attached to the pedicle screws for correction of concavity illustrated in FIGS. 21b, 22 and 23a.

FIGS. 44a and 44b show an embodiment where the extenders used for correction of the concavity are obtained by an extension of the flanges facing each other that define housing between them for implant of the second corrective rod.

Finally

DETAILED DESCRIPTION OF THE DRAWINGS

Figure 5:
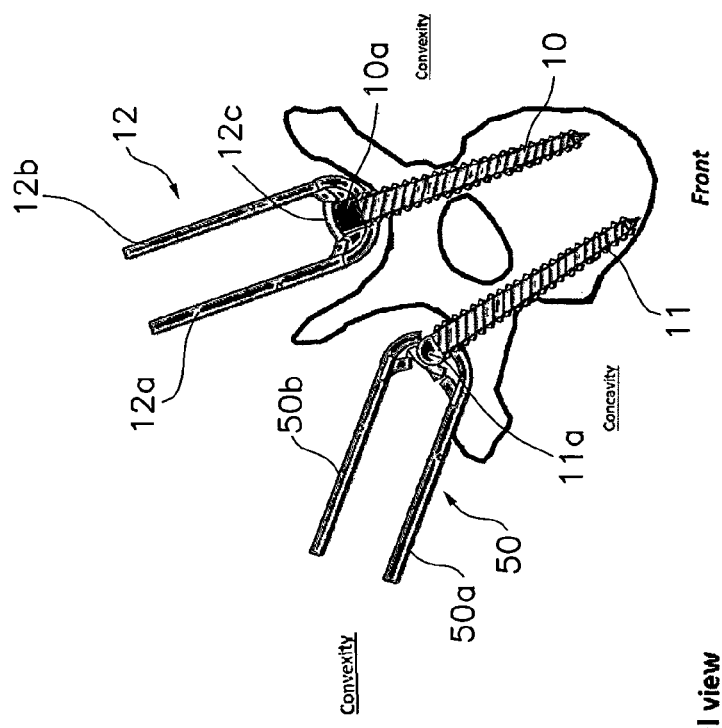
FIG. 5 illustrate the anchoring to the vertebra of FIG. 4 of two anchoring elements in the form of pedicle screws as per the invention with two corresponding receiving portion for attachment of the alignment elongate members or extenders, said receiving portions being pivotable in a single plane: sagittal for the pedicle screws for correction of the convexity side of the deformation, and in a single transverse plane, perpendicular to the previous sagittal plane, for the pedicle screws of the left side in the drawing, for correction of the concave part of the spine deformation.
Figure 4:
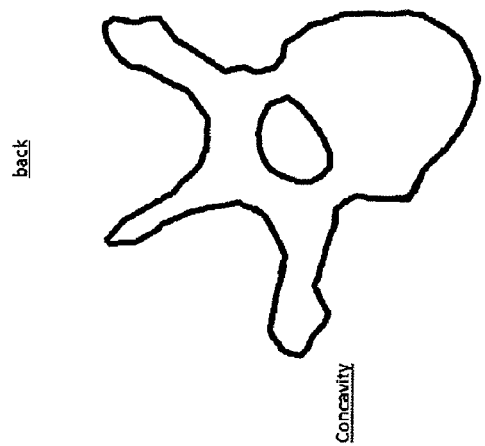
FIG. 4 is a schematic axial view of a vertebra affected by scoliosis in which convexity and concavity areas have been indicated.
Figure 3:
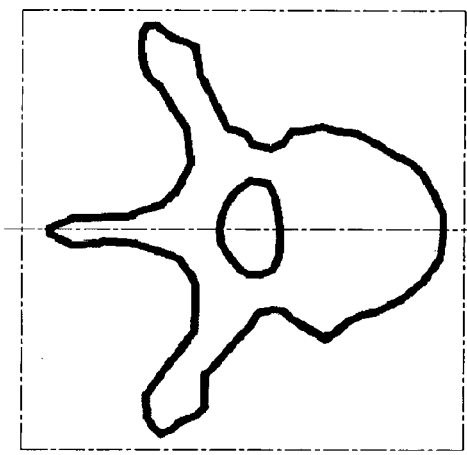
FIG. 3 is a schematic axial view of a normal vertebra.
Figure 9:
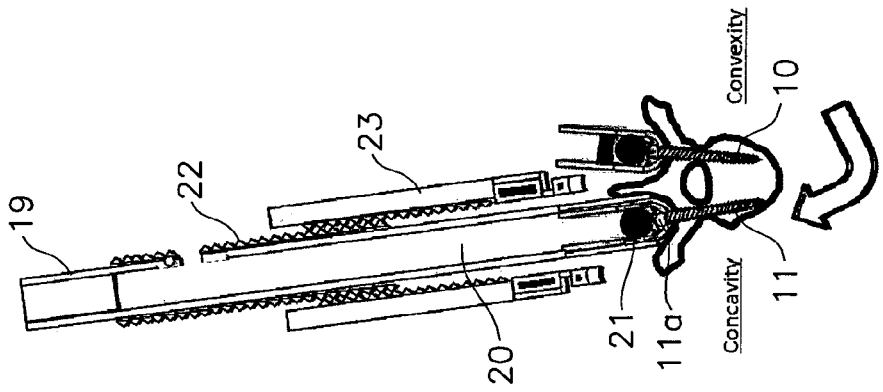
FIG. 9 illustrate the lowering of a ring pushing the second corrective rod to their final position to be fixed to the head of the second pedicle screw, as previously detailed.

FIG. 5 illustrates the principle of this invention, i.e. the use of pedicle screws: first pedicle screw 10 and second pedicle screw 11. As better detailed in FIGS. 11a and 11b receiving part 12 attached to pedicle screw 10 is pivotable in a single sagittal plane to allow for a correction occurring mainly in a transversal plane of the convexity. This pivoting movement differs from pedicle screw 11 for the convexity (see FIGS. 12a and 12b) where receiving part 50 is pivotable in a transverse plane perpendicular to said sagittal plane to allow for a correction of the concavity of the internal part of the deformed spine, said correction occurring mainly in a sagittal plane.

Pedicle screws of FIG. 5 comprise a threaded shaft 10, 11 and a head 10a, 11 a. As can be seen in FIGS. 5 to 10 said head 10a, 11a has two sections which are located opposite to each other and which have spherical outer surface and confronted to said two opposite spherical surfaces of the head two directly opposed shaped surfaces are defined. Receiving part 12 part has a housing 12a with two opposite spherical concave parts and two opposite shaped parts, so that depending on the position of the head of the anchoring member a pivotal movement in a single plane of the receiving member 12 with regard to said head 10a, 11a is allowed, said single plane being selected from a sagittal plane for said first bone anchoring element (allowing correction in a transversal plane) and from a medial plane or transversal plane for said second bone anchoring element (allowing correction in a sagittal plane).

While pedicle screws 10, 11 of FIG. 5, with a head 10a, 11a, and receiving part 12, 50 pivotally connected allowing pivoting in a single plane to be selected are know in the art, previous art does not disclose using two of them as proposes this invention, in association with extenders of a different structure for correcting both convexity and concavity parts of the spine curvature (refer to FIG. 1 and FIGS. 11a, 11b and 12a, 12b for understanding of the cited differentiated areas).

Receiving part 12 has in a preferred but not limitative embodiment a pair of elongated flat flanges 12a and 12b facing each other where proximal portion of alignment elongated members or spacers is secured. Receiving part also includes a portion 12c pressing on the head 11 for retention. Flanges 12a and 12b can alternatively be shorter.

FIG. 6 show tubular extender 13 for correction of the convexity attached by a proximal end portion to flanges 12a, 12b of receiving part 12 pivotally connected to the screw 10 for correction of convexity. Extender 13 has a longitudinal slot 14 allowing insertion of first corrective rod 15 to be implanted in the patient. The tubular extender 13 also includes near its distal end a retaining member 16 including a passage 16a for insertion therethrough of centering rod 17. A coaxial sleeve 18 intended to push (by hammering it) the corrective rod 15 to their final position (see FIG. 7) within the housing of receiving part 12 also appears in this FIG. 6.

Tubular extenders 13 will move only on a single sagittal plane due to the fact that they are attached to the screws 10. They are formed by two tubes slotted. The first short tube or retaining member 16, allows the introduction of a centering rod 17 to realign vertebras V on a same axis. The second slot 14 of extender 13 is reserved for the first corrective rod 15 that is introduced pre-molded, and descended by impactation towards housing provided by receiving part 12, to avoid pullout forces. This maneuver will result mainly in transverse plane realignment.

FIG. 7 show the first corrective rod 15 placed near the head 10a of the pedicle screw 10, after the coaxial sleeve 18 being lowered, by impaction, for example by using a hammer or similar member. Note that the centering rod 17 has been removed, once the first corrective rod 15 has been introduced into the housing on the head of the screw. However the first corrective rod 15 is still not fixed to said head to allow correction of the concavity.

Figure 8:
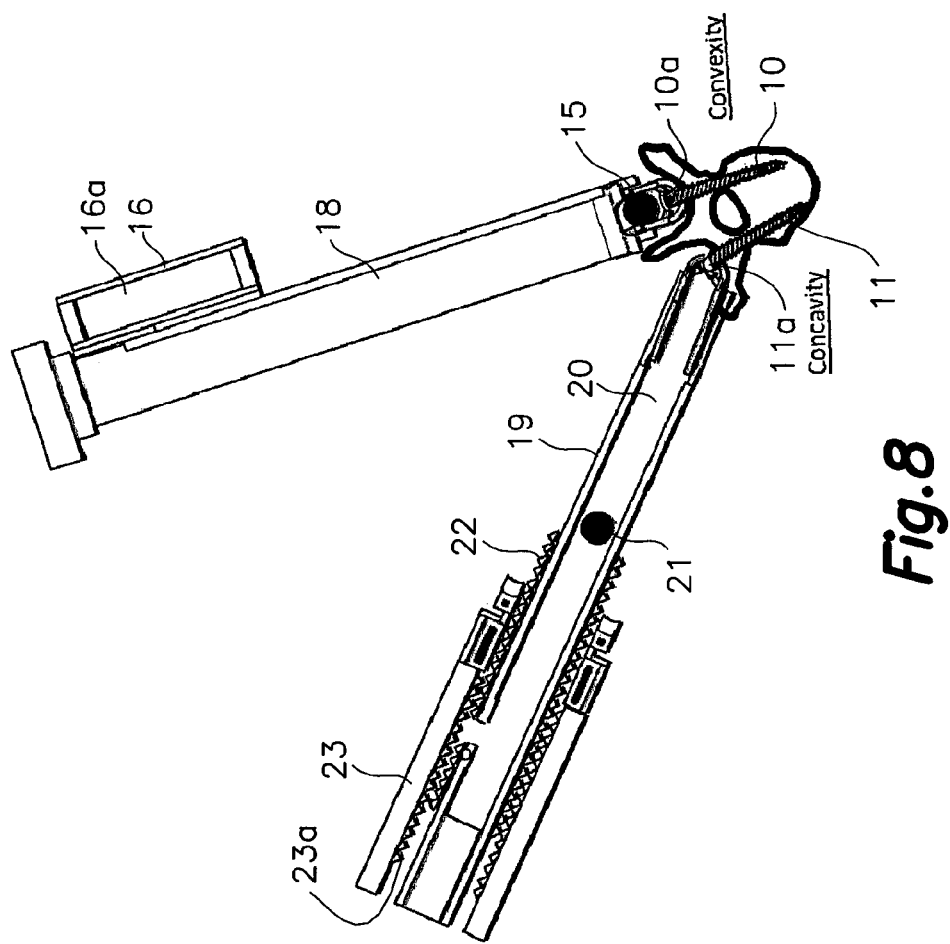
FIG. 8 shows the placement of an extender (in cross-section) of a different structure to the receiving portion pivotally connected to the head of a pedicle screw for correcting the concavity.

FIG. 8 further illustrate the placement of a tubular extender 19 for correction of concavity fastened to the flat flanges 50a and 50b of the receiving part 50 pivotally connected to the head 11a of pedicle screw 11. This tubular extender also is provided by a longitudinal slot 20 allowing insertion of second corrective rod 21. Tubular extender has an external threaded portion 22 and a ring with an inner threaded part 23a that is coupled to this tubular member 19, in order to progressively push by screwing the second corrective rod 21, lowering it to their final position (see FIG. 9).

Figure 10:
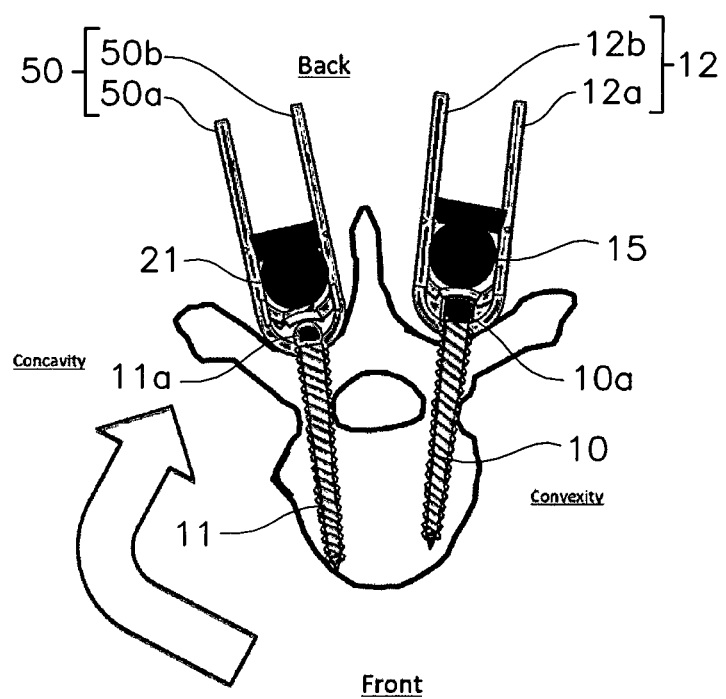
FIG. 10 shows in a schematic view the final correction of the spine deformity with the two first and second corrective rods fixed (implanted) attached to the respective pedicle screws. The compression of the rod against the pivotable mechanism locks the system avoiding any further movement of the head on relation to the pedicle screw

FIG. 10 illustrates the final position of the two corrective rods 15, 21 that remain implanted in the patient after removal of the extenders and fixing of said corrective rods 15 and 21 to the corresponding heads 11 and 11a of the corresponding pedicle screws 10 and 10a.

FIG. 11 illustrates placement of the screws 10 on different vertebrae V of the curved spine to be corrected, and FIG. 11a illustrates a cross section indicating the limitation of movement of flanges 12a, 12b in a single sagittal plane allowing for insertion of the rods 15 and 17 (see arrows in FIG. 11b) so that correction in a transversal plane is allowed as the first corrective rod 15 attached to flanges 12a, 12b, is moved in such a transversal plane pushing the vertebra and screw 10 follows said movement as it can not pivot in such a direction (see FIGS. 5, 6 and 11a).

FIG. 12 illustrates placement of the screws 11 on different vertebrae V of the curved spine to be corrected, and FIG. 12b illustrates a cross section indicating the limitation of movement of flanges 50a, 50b in a single medial or transverse plane allowing for insertion of the rod 21 (see arrows in FIG. 12a) so that correction in a sagittal plane is produced as the extender 19 is translated in such a transversal plane and screw 11 follows said movement as it can not pivot in such a direction (see FIG. 11a).

Figure 13:
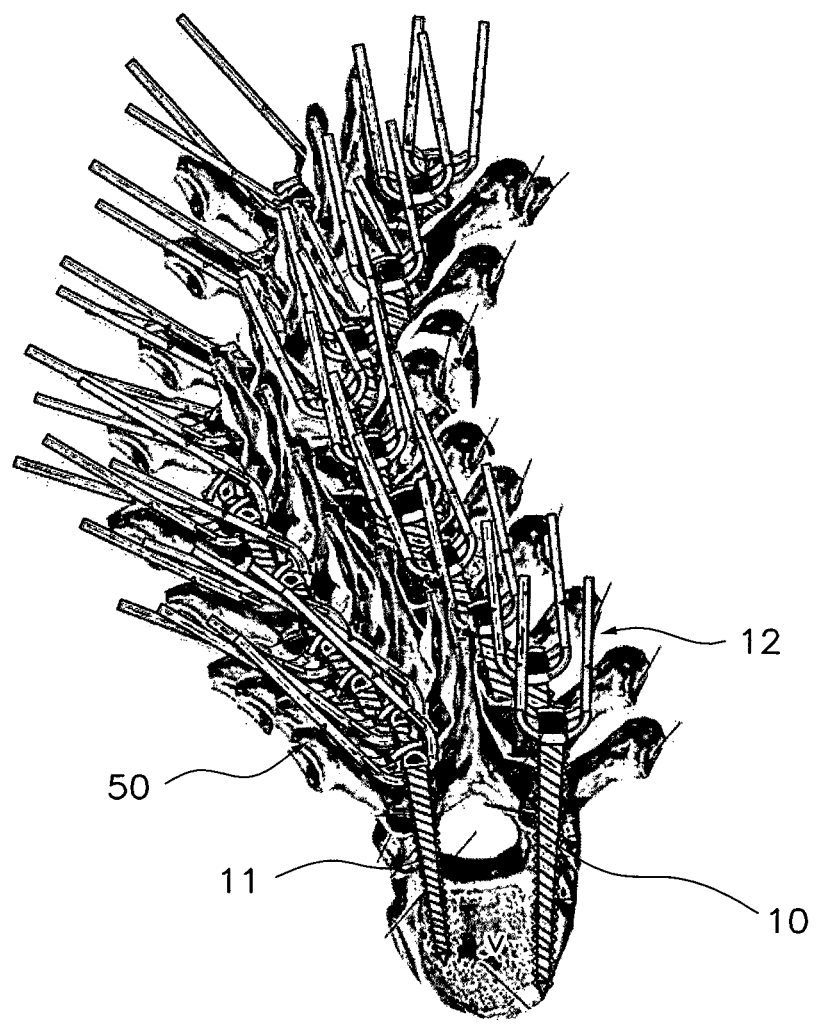
FIG. 13 is a drawing illustrating the placement of both pedicle screws for correcting the convex and concave sides of the spine curvature of FIG. 1.

Finally in FIG. 13 both screws 10 and 11 are placed in the different vertebrae of the spine curve to be corrected without the extenders.

Figure 15:
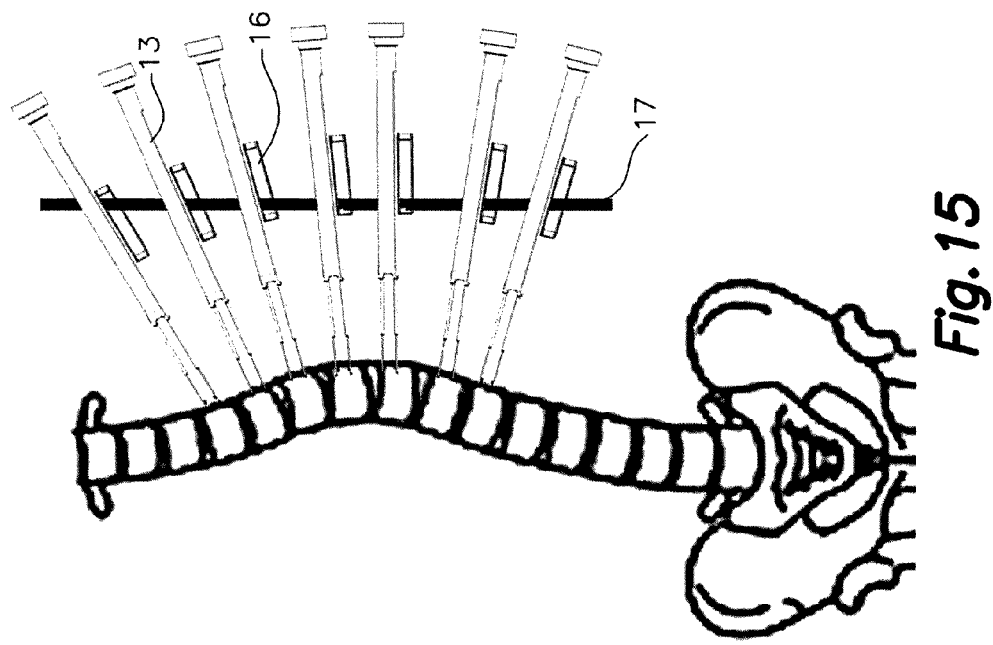
FIG. 14 and FIG. 15 illustrates over radiography of a patient with spine scoliosis placement of extenders and first reduction/corrective rod for correction of convex side of spine.
Figure 14:
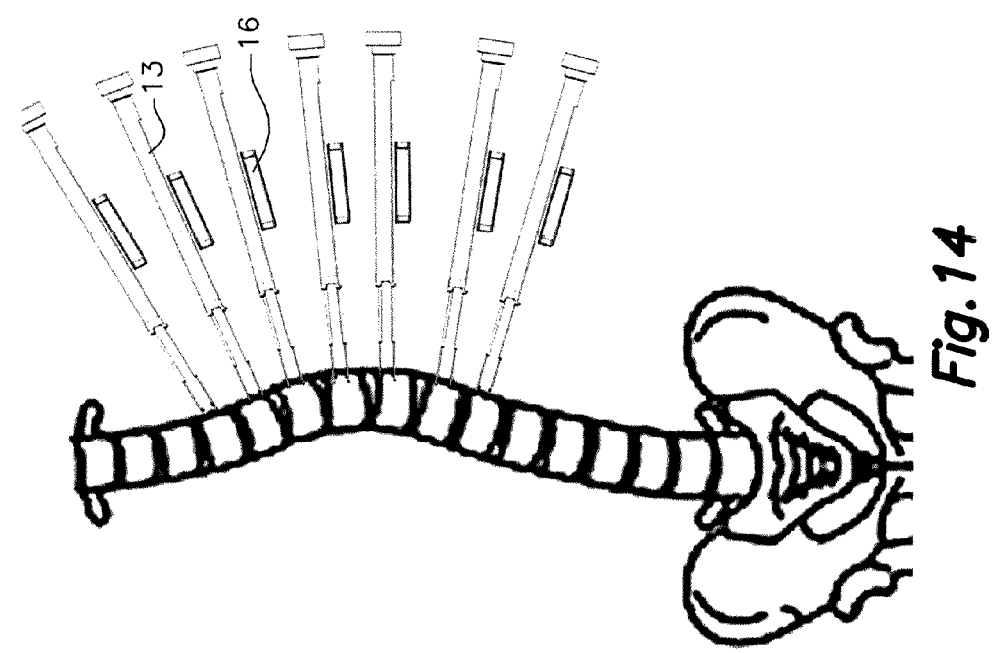
Figure 16:
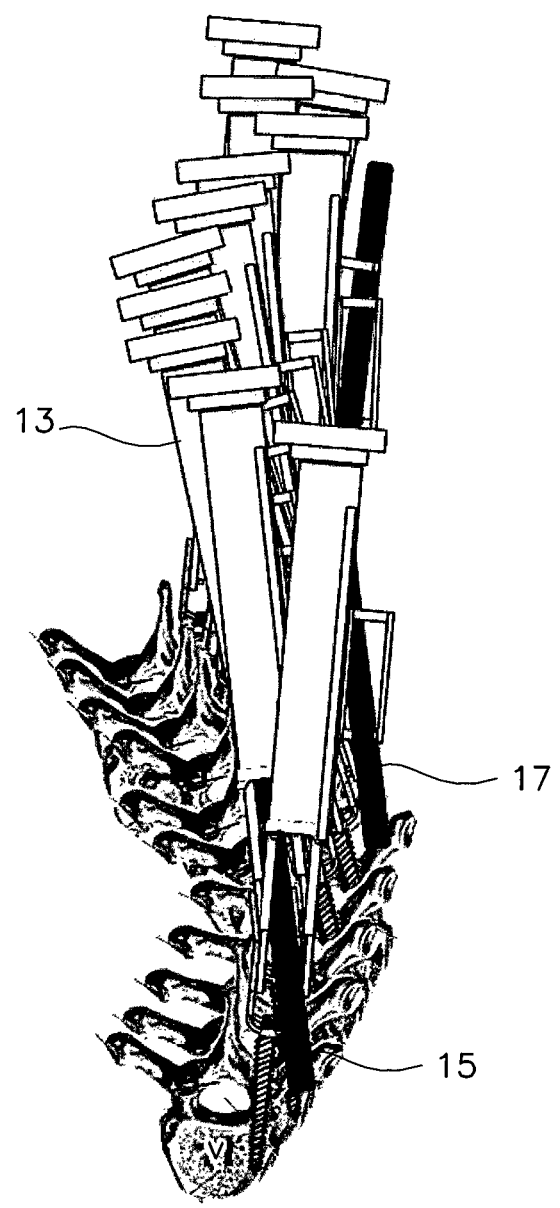
FIG. 16, illustrate placement of second corrective rod (to be implanted finally in the patient) placed through the slot of the extenders partially aligned by centering rod.

FIG. 14 show the placement of the extenders 13 provided as auxiliary elements in the correction of the convexity shown on radiography of the spine of a patient and FIG. 15 is an equivalent figure showing the extenders and the centering rod 17 placed through the slot of retention member 16 of extenders 13. FIG. 16 depictures in a perspective view centering rod 17 and first corrective rod 15, interrelated with extenders 13 and respectively passed trough slots 14 and slot 16a.

Figure 17A:
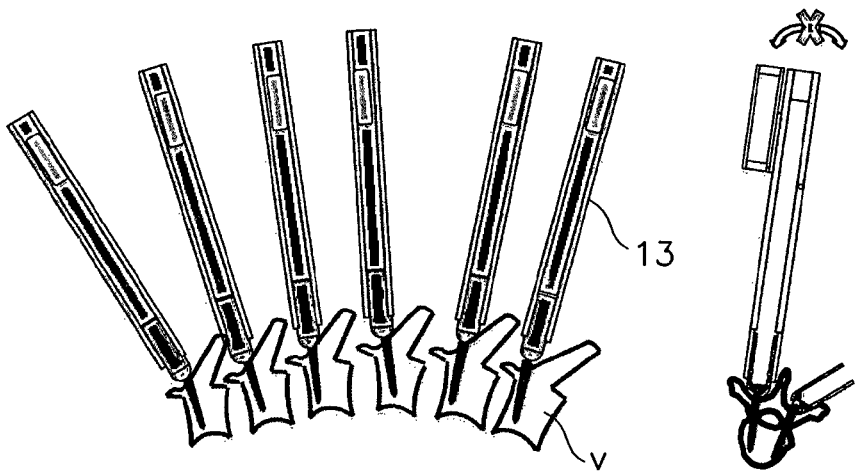
FIG. 17a (lateral view) illustrates the situation of the extenders before placement of the centering rod evidencing the kyphosis of the vertebrae and FIG. 17b illustrate the situation after placement of said centering rod obtaining a flattening of the kyphosis and shortening of the extension of the deformed section of the spine.
Figure 17B:
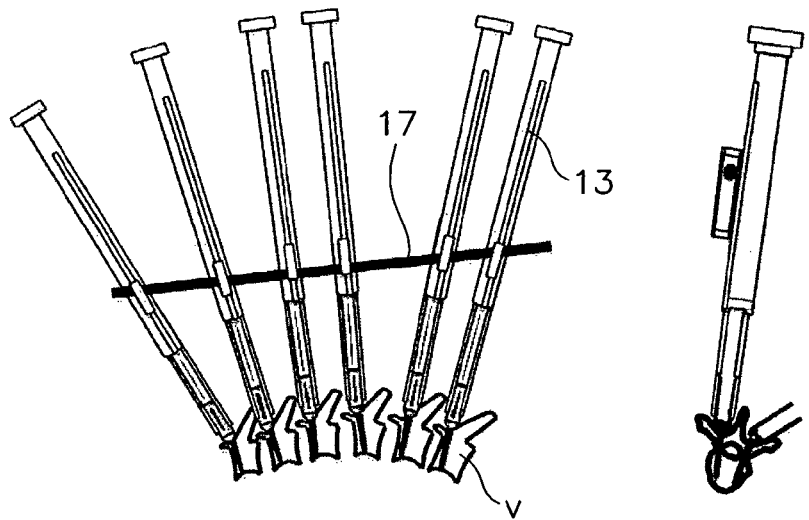

FIGS. 17a and 17b show placement of the centering rod 17 associated to extenders 13 for correction of the convexity. FIG. 17a evidencing the kyphosis of the group of vertebrae V in the convexity and FIG. 17b showing the flattening of the kyphosis and shortening of the posterior perimeter space of said extenders that starts once the centering rod 17 is attached to extenders 13.

FIGS. 18*a* and 18*b* are continuation to previous two figures and further depicture the placement of the first corrective rod 15 at a distance of vertebrae V and near the head of screws 10, but still not secured to them in order to allow correction of the convexity as following disclosed. Note the progressive flattening and shortening of the posterior perimeter.

FIG. 19 show the placement of the extenders 19 for correction of the concavity attached to screws 11 on the vertebrae of the concavity side depictured on a radiography of a patient.

Figure 1:
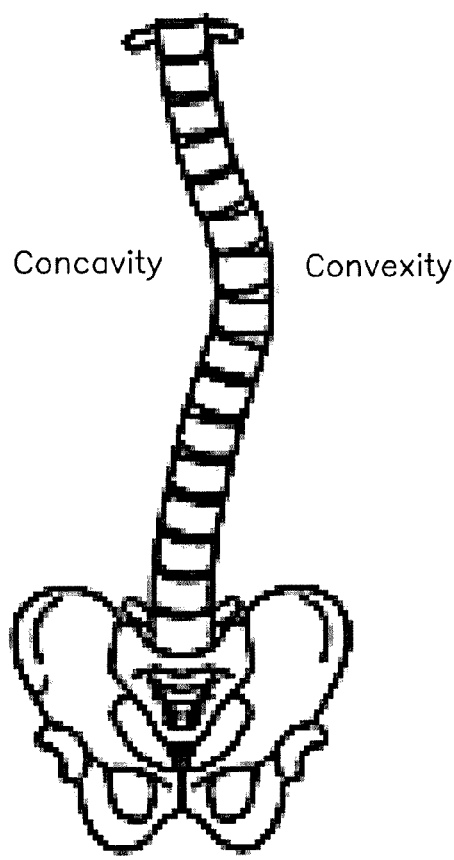
FIG. 1 is an image corresponding to radiography of a frontal view of a patient with scoliosis in which concavity and convexity sections of the deformed spine have been indicated.
Figure 2:
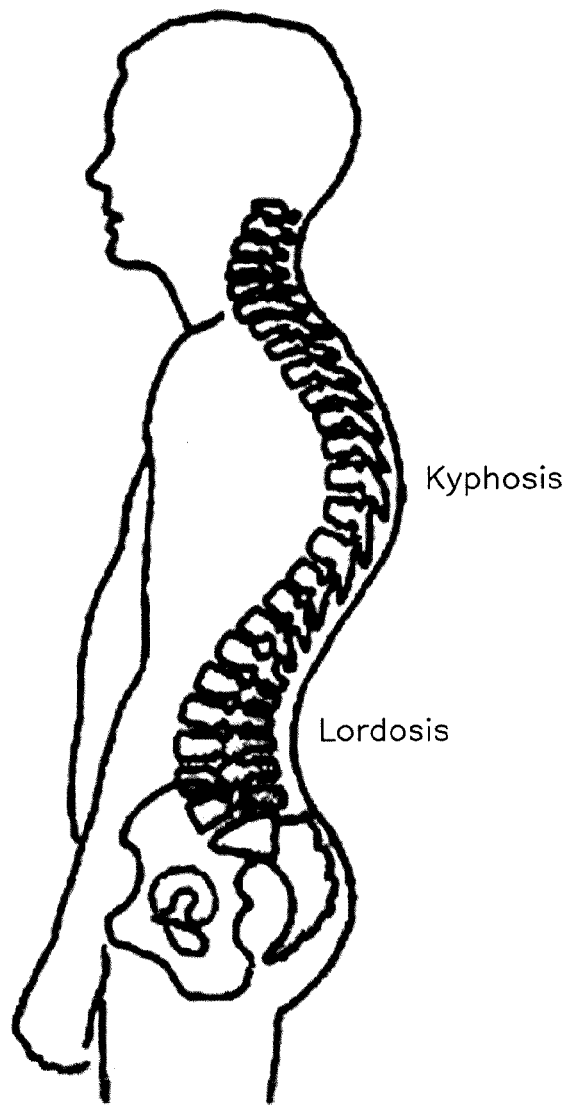
FIG. 2 is radiography of same patient corresponding to a lateral view.
Figure 20:
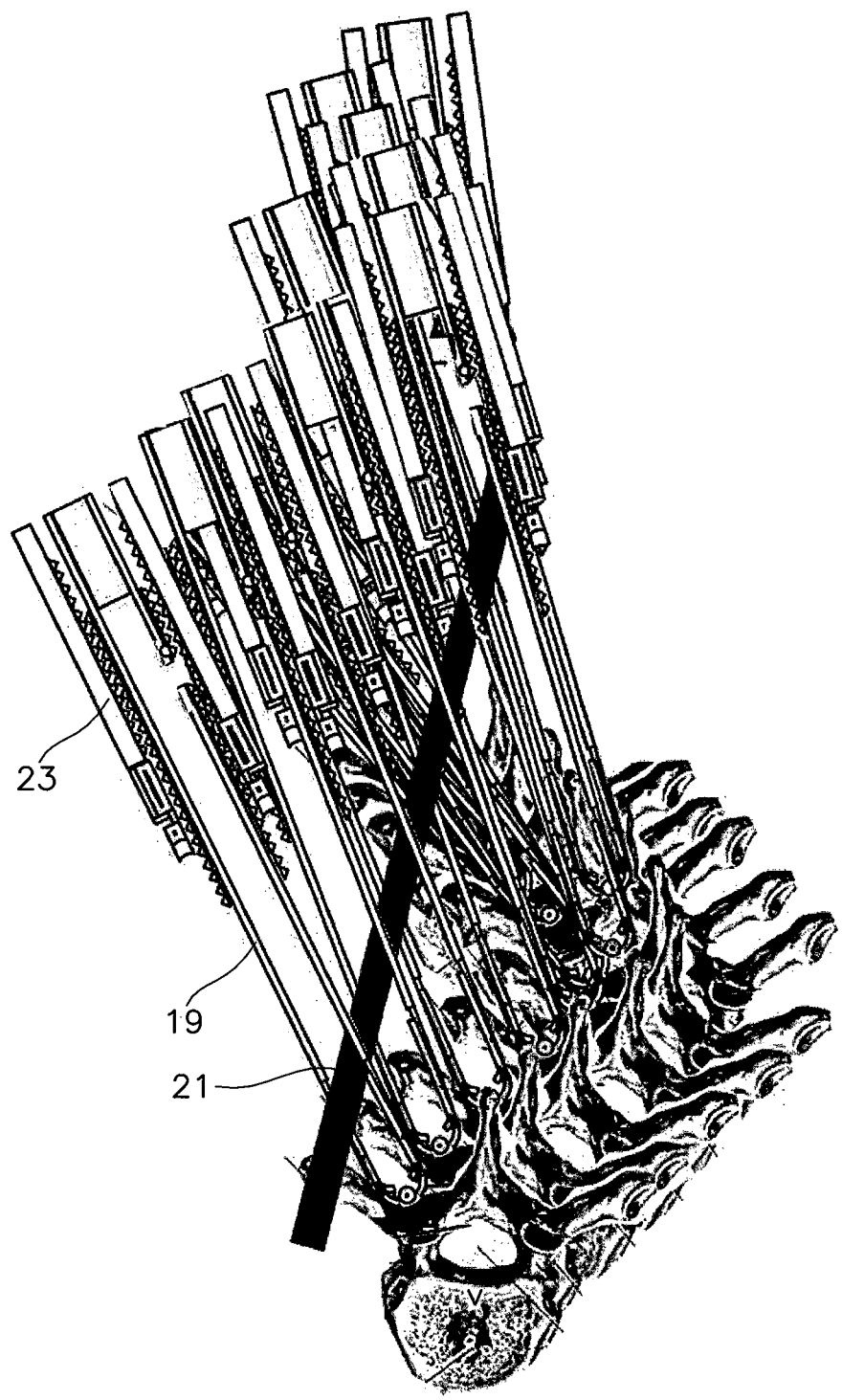
FIG. 20 illustrate placement of a second corrective rod or kyphosis rod (to be implanted finally in the patient) placed through the slot of the extenders of FIG. 19 for correction of concave side of spine.

FIG. 20 show in great detail extenders 19 and second corrective rod 21 (for kyphosing correction) as well as the threaded ring 23, intended for correction of the concave side (always with reference to FIG. 1 of the drawings).

FIG. 21*a* explains in a lateral view the placement of the second corrective rod 21 through longitudinal slot of extenders 19 in an initial position with flattening and loss of kyphosis.

FIG. 21*b*, show in a lateral view the pushing of the second corrective rod 21, lowering it by threading the ring or nut 23 on the tubular extender 19 provided as detailed with an external threaded surface. In this figure also some spacers 24 are illustrated provided at the distal ends of extenders 19 for correcting the concavity designed to prevent or at least decrease "pull-out" forces on the concave screws 11. Additionally placement of the kyphosis spacers 24 means an increasing of outer perimeter.

FIG. 22 show in a lateral view a complete group of said spacers 24 connecting distal ends of extenders 19, therefore increasing kyphosis and lengthening of the posterior perimeter and FIG. 23*a* details placement of the second corrective rod 21, down against the head 11*a* of the pedicle screws 10*a* for the concavity, by threading on the extenders 19 threaded rings, with still the spacers coupled to distal ends of spacers 19, and with telescopically extension of them during the lowering of definitive rod 21.

FIG. 23*b* show in a lateral view how locking nuts are introduced through the extender to lock the rod to the screw head.

the second corrective rod 21 at its final position firmly secured against heads 11*a* of pedicle screws 11 for correction of the concave side, with removal of extenders 19.

FIGS. 24*a* and 24*b* show in a lateral view initial and final position of the second corrective rod 21, while evidencing kyphosis reconstitution and increase of the length of the posterior column.

Figure 25C:
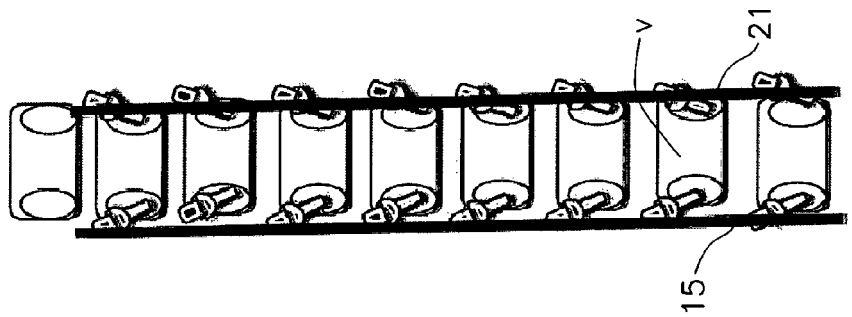
FIGS. 25a to 25c show in a frontal view and in a schematic way the orientation of the vertebrae along the implementation of the system for a global three-dimensional correction of the curvature of the spine of this invention. Final situation in FIG. 25 c show the two reduction rods implanted in the patient the rod for the convexity (left side of Fig. c) being the last one to be fixed to the corresponding pedicle screws.
Figure 25B:
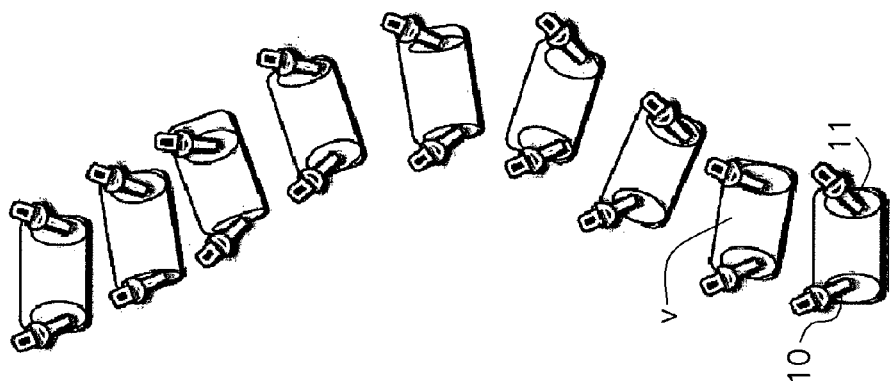
Figure 25A:
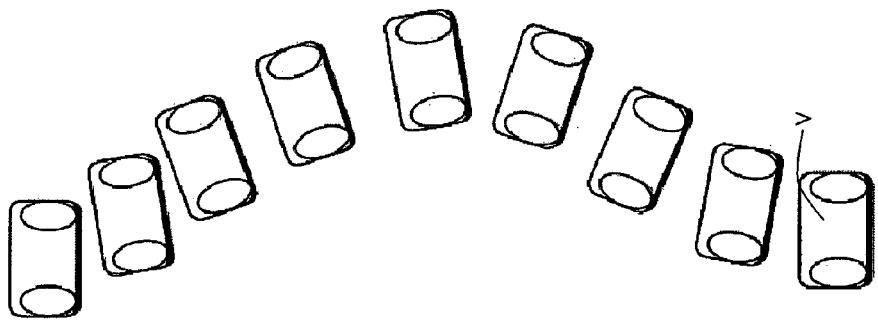

FIGS. 25*a*, 25*b* and 25*c* diagrammatically illustrate as per a coronal view the initial situation of the curved spine, the vertebrae of said curved spine provided with pedicle screws 10, 11, and final result with corrective rods 15 and 21 firmly secured to heads 10*a* and 11*a* of said pedicle screws 10, 11, i.e. implanted on the patient corrected spine.

FIG. 26 is a side elevation view of tubular extender 13 with longitudinal slot 14 for receiving first corrective rod 15, comprising a tubular upper portion 16 providing a retaining member for reception of the centering rod 17 passed through slot 16*a*.

FIG. 27 shows in an upper view both tubular members 13 and 16 side connected through bridge 25.

Figure 28:
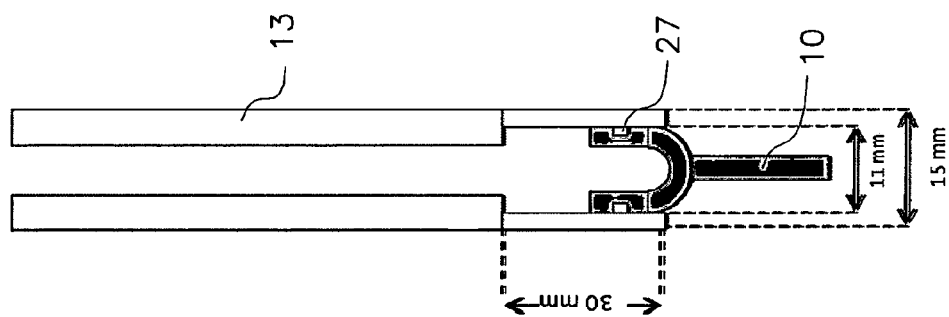
FIG. 28 is a detail of connection between proximal end of the tubular element or extender of FIG. 26 and receiving part pivotally connected to the head of a pedicle screw.
Figure 32D:
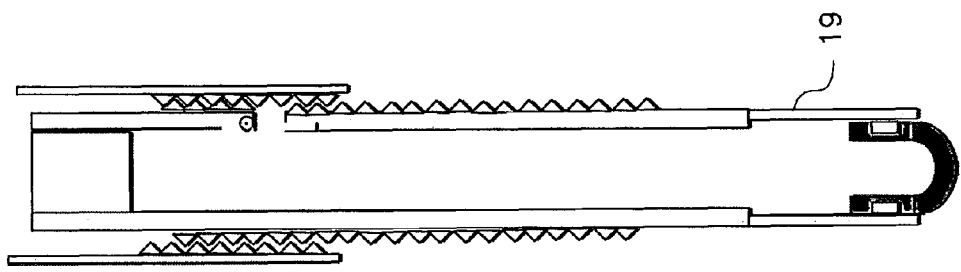
FIG. 32d illustrate placement of a ring that is threaded over a threaded external part of the tubular element to push the reduction rod to its final place.
Figure 32C:
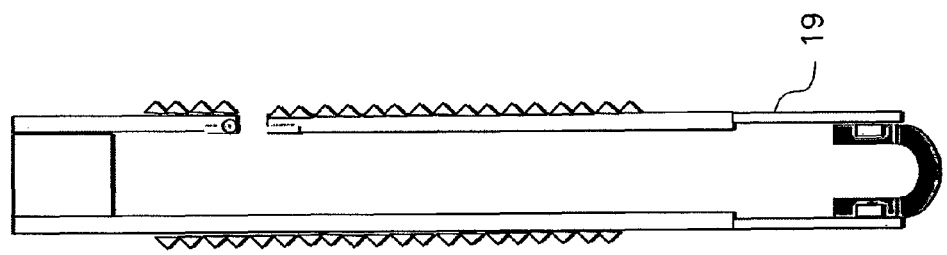
FIGS. 32a to 32c are illustrative views of tubular alignment element or extender associated to the receiving part of pedicle screw for correction of the kyposis (concavity), illustrating a portion of the tubular member connected by an articulation to be separated (FIG. 32b) to catch (FIG. 32c) a section of said receiving part.
Figure 32B:
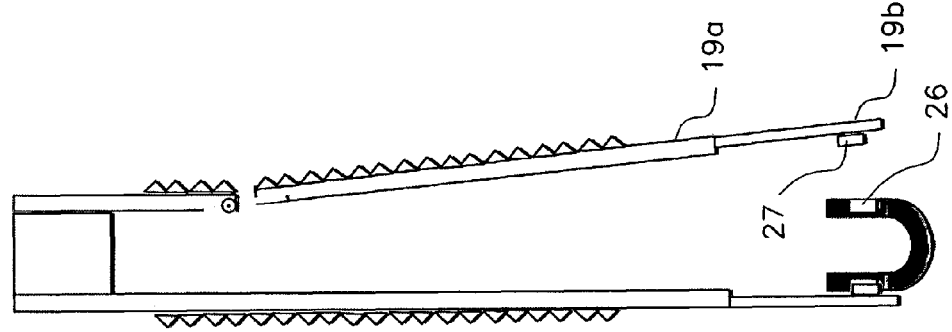
Figure 32A:
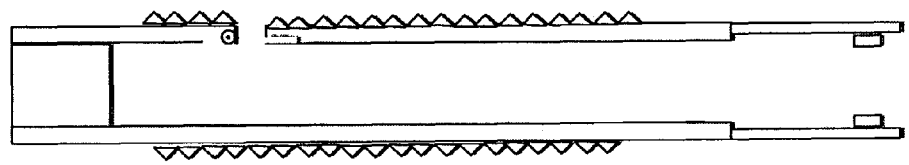

FIG. 28 show the connection of the end of tubular extender 13 to the flat flanges 12*a* and 12*b* of receiving section pivotally articulated to the head 10*a* of pedicle screw 10 for correcting the convexity. Same structure is provided for attaching extender 19 to the flat flanges 50*a*, 50*b* of receiving section pivotally articulated to the head 11*a* of pedicle screw 11. To this end said flat flanges 12*a*, 12*b* or 50*a*, 50*b*, include an opening 26 (see FIG. 32*b*) where an internal lug 27 is received providing a fastening.

Figure 29:
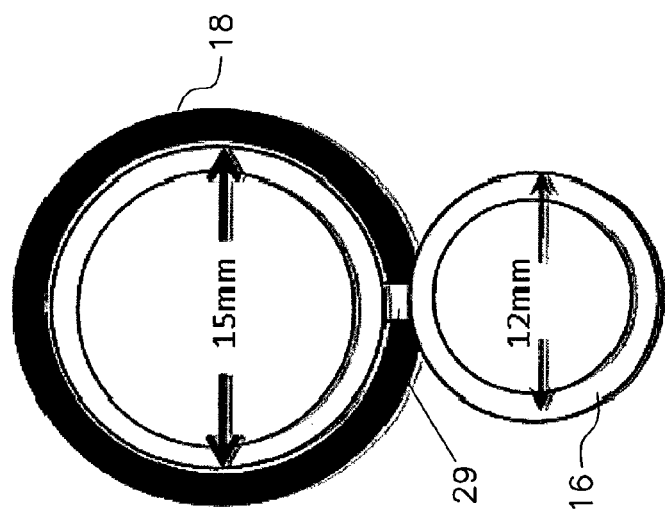
FIG. 29 is a cross section illustrating placement of the sleeve intended to place by impact first corrective rod for correction of the convexity.

FIG. 29 is equivalent to FIG. 27 but with a sleeve 18, with a peripheral longitudinal slit 29, put on the tubular extender 13, coaxially embracing it.

Figure 30C:
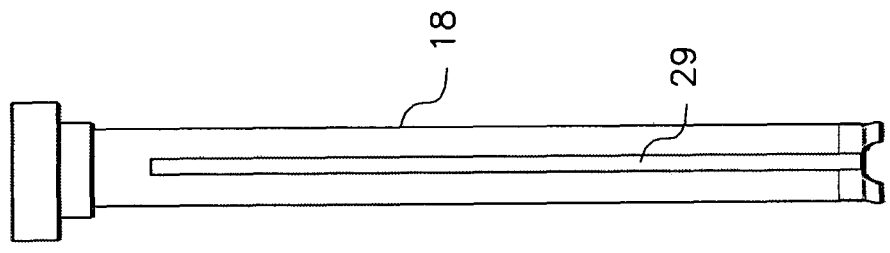
FIGS. 30a and 30c are side views of the cited sleeve and FIG. 30b is a cross section thereof.
Figure 30B:
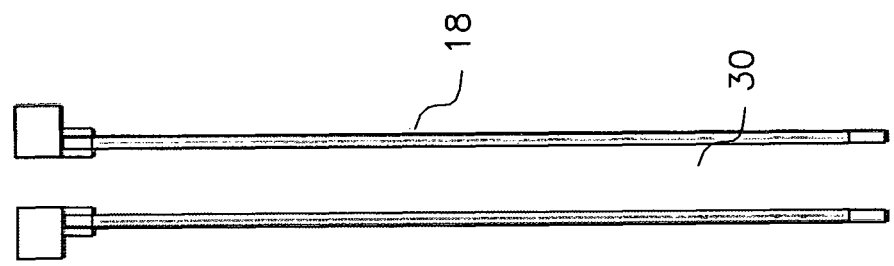
Figure 30A:
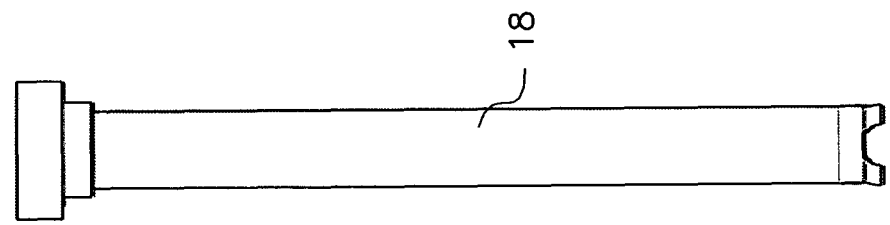

FIGS. 30*a*, 30*b* and 30*c* illustrate the sleeve 18 with longitudinal slit 29 and central longitudinal aperture 30. Note that the top and end of the sleeve are constructed in polyethylene of high density to allow for impaction of the sleeve (hammering) and contact with the first reduction rod without producing metal debris.

Figure 31:
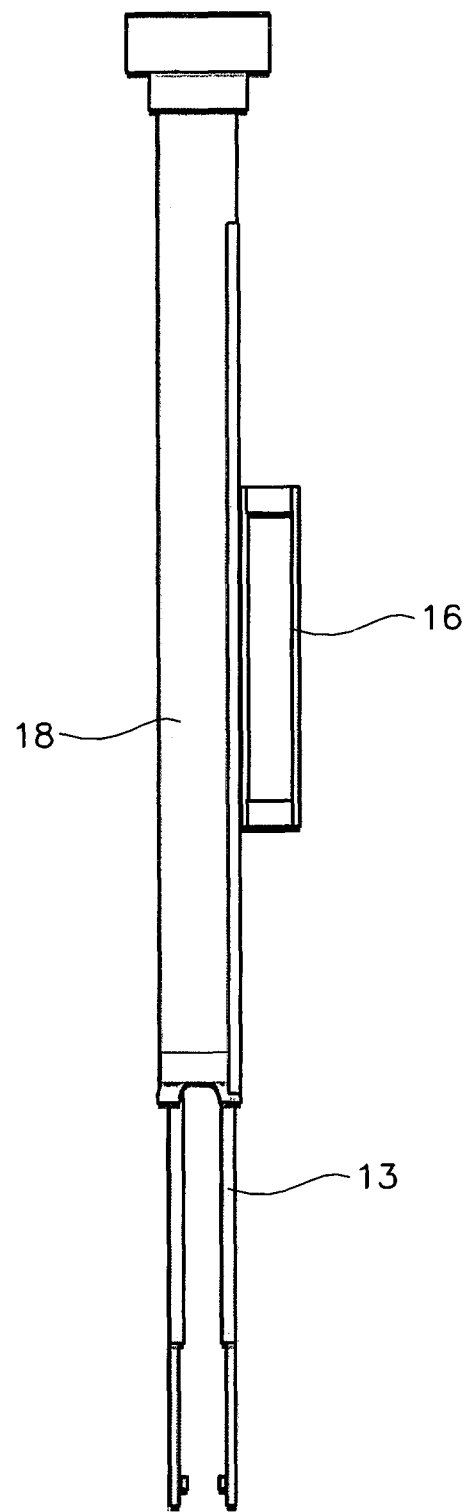
FIG. 31 is a front view illustrating placement of the sleeve over the tubular extender of FIG. 26

FIG. 31 depictures the sleeve 18 placed on the tubular extender 13 in order to push down the first corrective rod 15 as already depictured in FIGS. 6 and 7.

FIGS. 32*a* to 32*d* refer to another embodiment of the tubular extender 19 (also applicable to extender 13) consisting in that a portion 19*a* of said tubular member 19 being articulated to an upper region of the tube in order an end 19*b* of the proximal part of the extender 19 permitting a separation (see FIG. 32*b*) to catch a section of said flat flanges 50*a*, 50*b* of receiving member 50 (in the example not elongated), to temporally fastening both said proximal ends 19*b*, 19*c* and flat flanges 50*a*, 50*b*. This particular construction facilitates securing of the extenders 19 (or 13) and removal thereof once the corrective rods 15 and 21 are located in their definitive corrective position.

Figure 33:
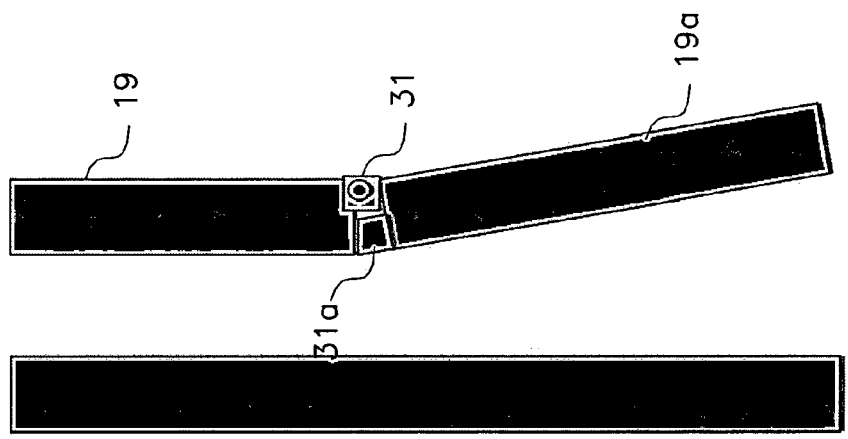
FIG. 33 is a detail of the articulation of part of the tubular member of extender of FIGS. 32a to 32c.

FIG. 33 is a detail of an embodiment of the articulation 31 of portion 19*a* of extender 19 with a stop 31*a*, limiting tilting (same structure is applicable to the extender 13.

Figure 34B:
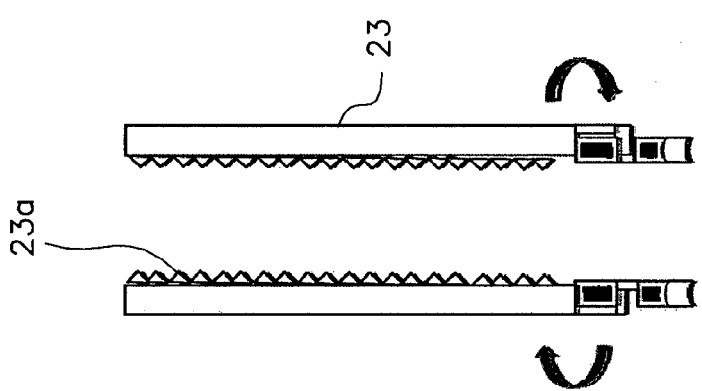
FIGS. 34a and 34 b are details of the tubular element or extender of FIGS. 32a to 32c and of the ring threaded over said tubular extender.
Figure 34A:
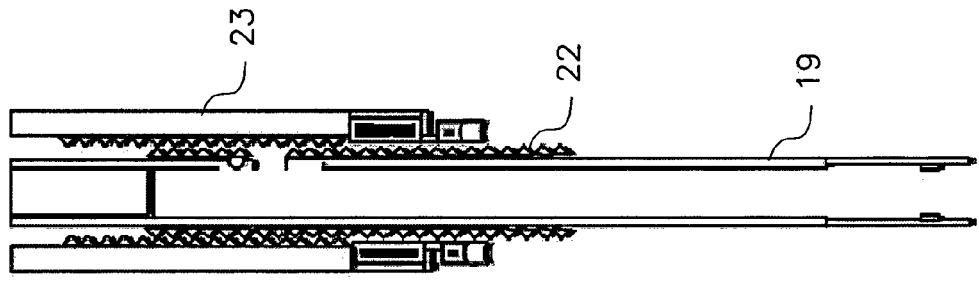

FIG. 34*a* detail construction of extender 19, with external threaded part 22 where a ring or nut 23 is placed in order to push the second reduction rod down until its final position, as previously disclosed by threading said ring 23.

FIG. 34*b* is an enlarged detail of ring 23 with inner threading. Note that the end of the ring is a free turning embolus finished in high density polyethylene (to avoid metal fiction and metal debris) to push the second reduction rod toward the screw head.

Figure 35A:
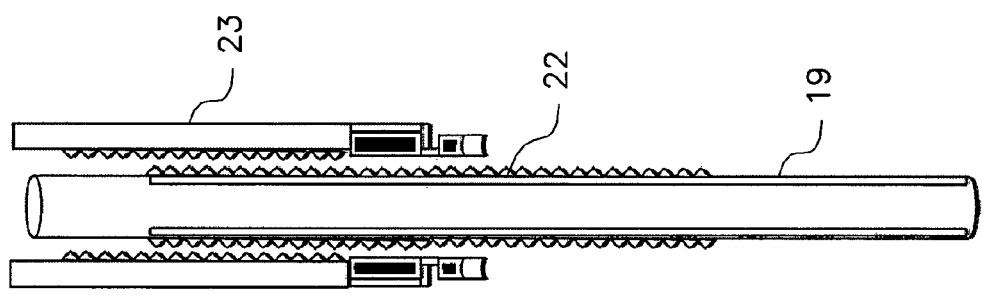
FIGS. 35a and 35b are further views of the tubular element or extender in association with its ring for displacement of the reduction rod.
Figure 35B:
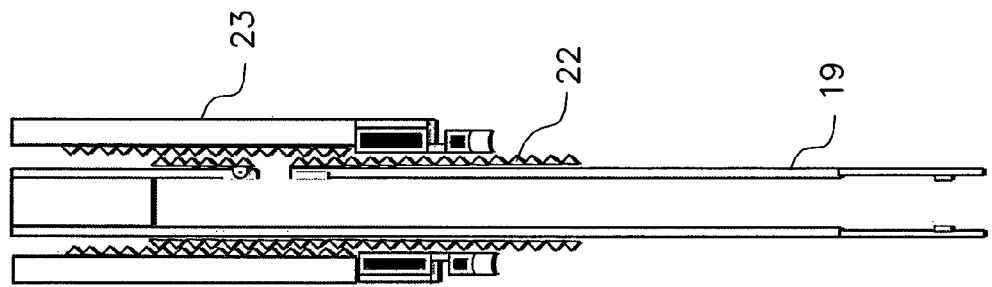

FIGS. 35*a* and 35 *b* depicture the extender 19 in association with ring or nut 23 as previously described in two lateral side views.

Figure 36A:
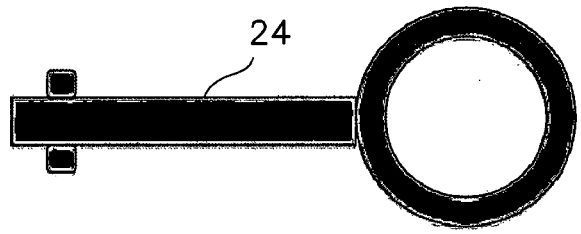
Figure 36B:
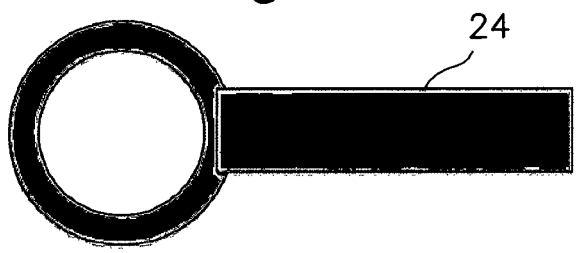
Figure 36C:
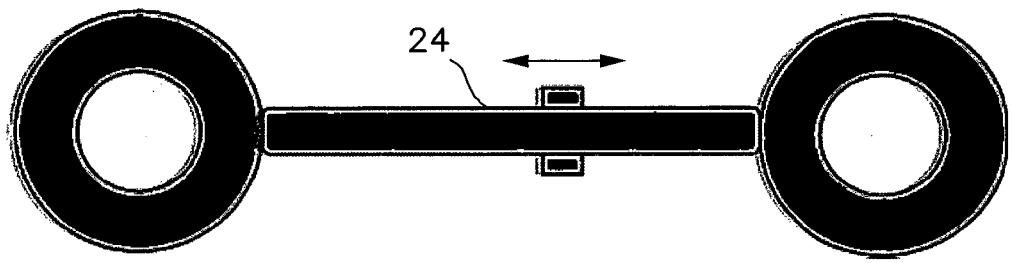
Figure 36D:
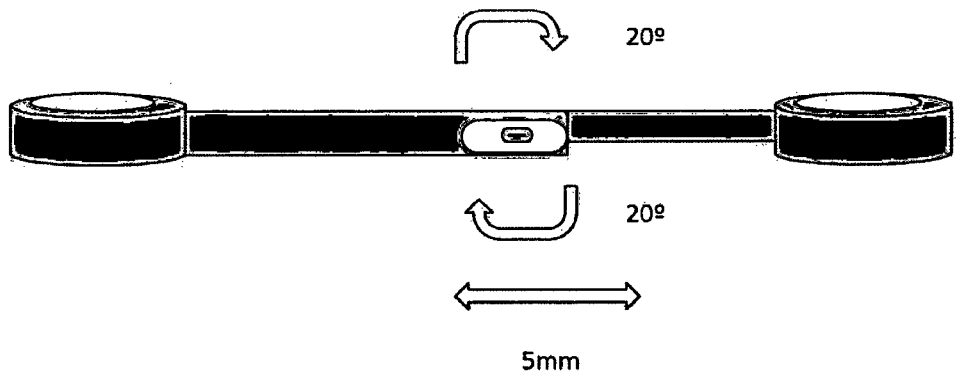

FIGS. 36*a* to 36*c* show one embodiment for a spacer 24, telescopically extendable intended to be associated to distal ends of extenders 19 as clearly shown in FIGS. 21*b*, 22 and 23 previously detailed.

Mention will be done in the following about calculation on preoperative molding of the rods and the definition of the spacer's length in the concavity which is an additional singularity of the system of this invention allowing systematizing the surgical treatment of spinal deformity.

No current system implements a preoperative calculation of the correction to be applied in each scoliotic patient. The method presented here provides a systematic preoperative calculation of the correction, this meaning that the correction to apply to each level of the spinal deformity can be selected and applied intraoperatively. With this system the longer scale correction is not anymore handmade, becoming predictable, measurable and could be calculated preoperatively. Surgical outcomes will be ameliorated producing obvious benefits for the patients.

The method for calculating the correction to be achieved with the surgery is made based on long-cassette preoperative antero-posterior and lateral spine radiographs used routinely for all patients going to undergo surgery. On these radiographs the exact deflections of convexity and concavity are calculated as well where to apply them to achieve the scoliosis correction.

Figure 37:
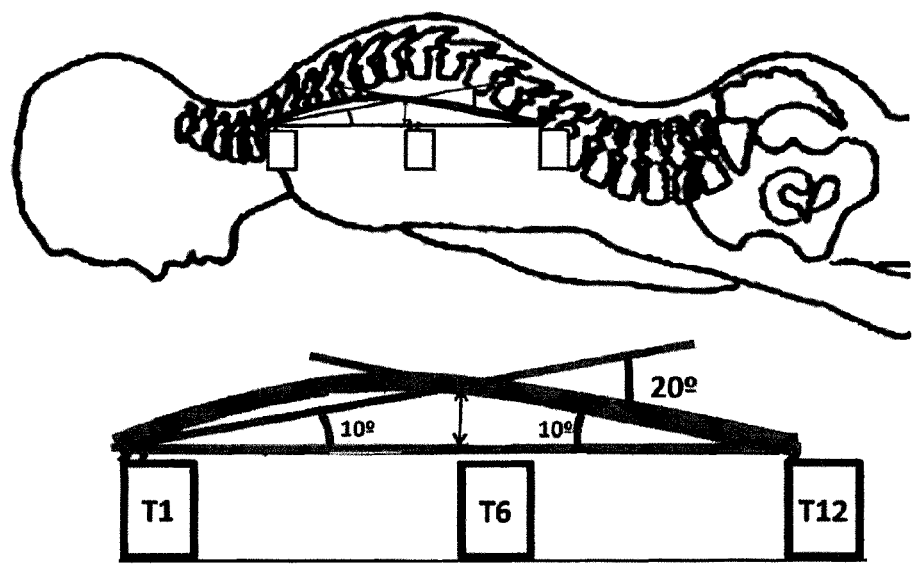
FIGS. 37 and 38 are illustrative views of the pre-operative procedure to prepare the preformed correction rod, to correct the patient's kyphosis and lordosis.
Figure 38:
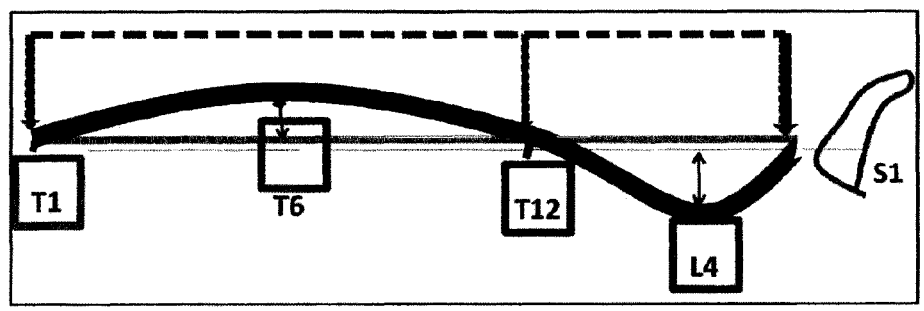

The calculation of molded deflection of the convexity rod (FIGS. 37 and 38) is made on the lateral preoperative radiography using the following methodical: the rod will be molded with 20° of kyphosis in the spine chest that is the lesser physiological value, with the apex T6 in the middle. To calculate the necessary deflection on the T6 on the lateral radiograph vertical height of the line connecting the middle of the rear end of the pedicles of T1 and T12 to the point where two lines cross leaving the vertices of the angles anterior superior T1 and T12 forming a 10° angle at the level of T6 and this produces the 20° of thoracic kyphosis.

Figure 39:
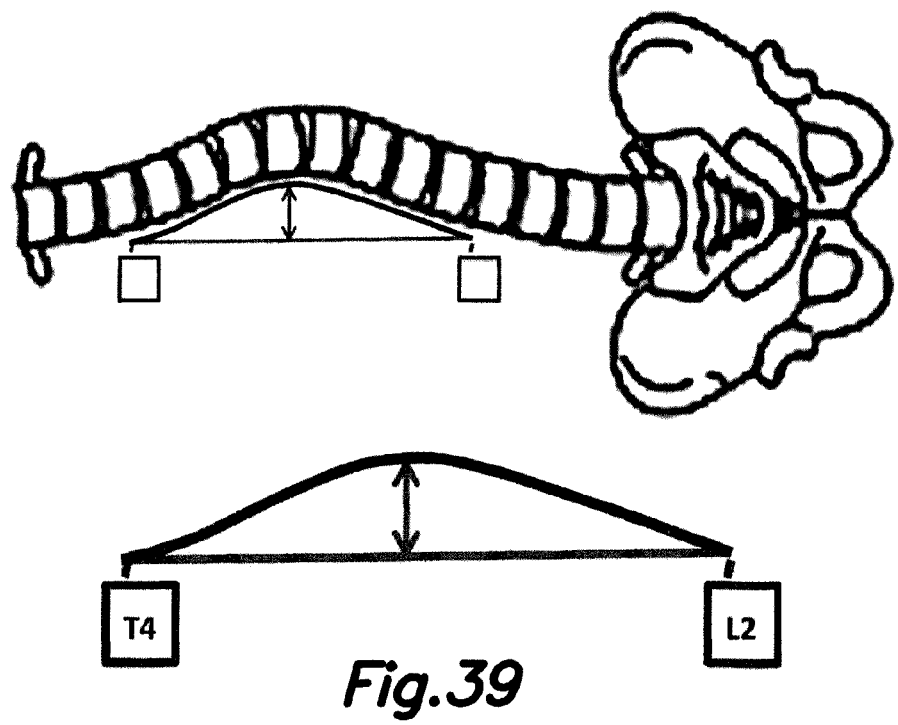
FIGS. 39 and 40 are illustrative views of the pre-operative procedure to prepare the preformed correction rod, to correct the patient's scoliosis.

In contrast the calculation of molding and deflection at the apex of the curve of the corrective rod for the concavity (FIG. 39), the calculations are made on the antero-posterior radiography measuring the vertical height extending perpendicular from the midpoint of the pedicle of the concavity of the apical vertebra of the scoliosis to the point of contact with the line joining the concavity pedicles of the vertebrae which ends should be fused.

Figure 40:
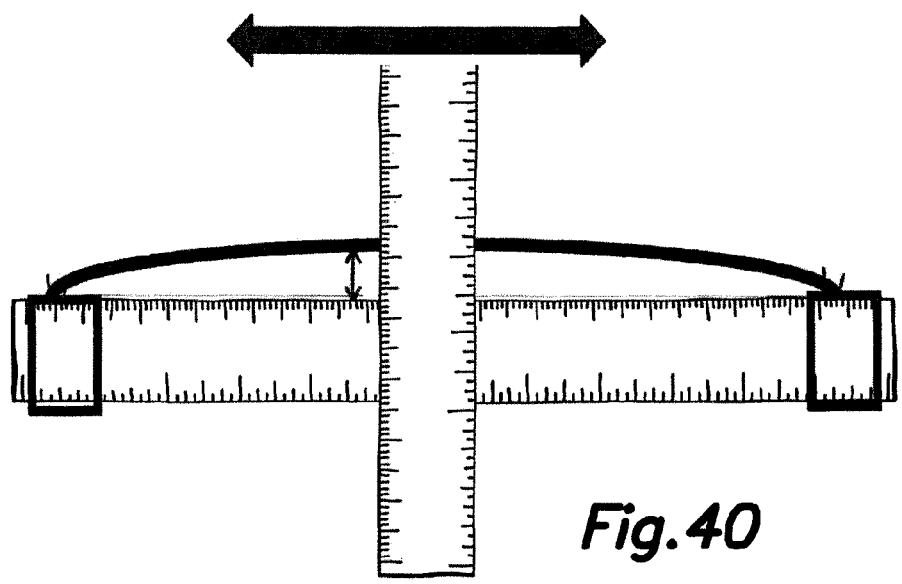

Measuring of the deflection of the corrective rod for the convexity and concavity requires the use of a measuring device consisting of two rules cross over each other with possibility of sliding (FIG. 40). These calculations can be implemented in a computer program that enable obtaining printed on the final shape of the corrective rods (to be implanted) for the concavity and convexity to the real dimensions of the patient, so that the surgeon can easily molded definitely rods for implanting in the patient, thereby achieving the planned correction by the surgeon. These corrective rods preformed preoperatively could be modified by the surgeon at any time if required intraoperatively As is done for calculation of the molded hollow rod, the calculation of the length of the spacers of the concavity of each level will be performed about the antero-posterior radiograph (FIG. 5). These spacers are critical because they decrease stresses at the time of placing the second reduction rod to definitive rod for the concavity completing the correction of the rotation and lordosis of the concavity, applying stresses on these screws that will be transformed, thanks to these spacers 24 from priority traction forces on other cephalo-caudal forces with a lesser risk for the patient.

Figure 42:
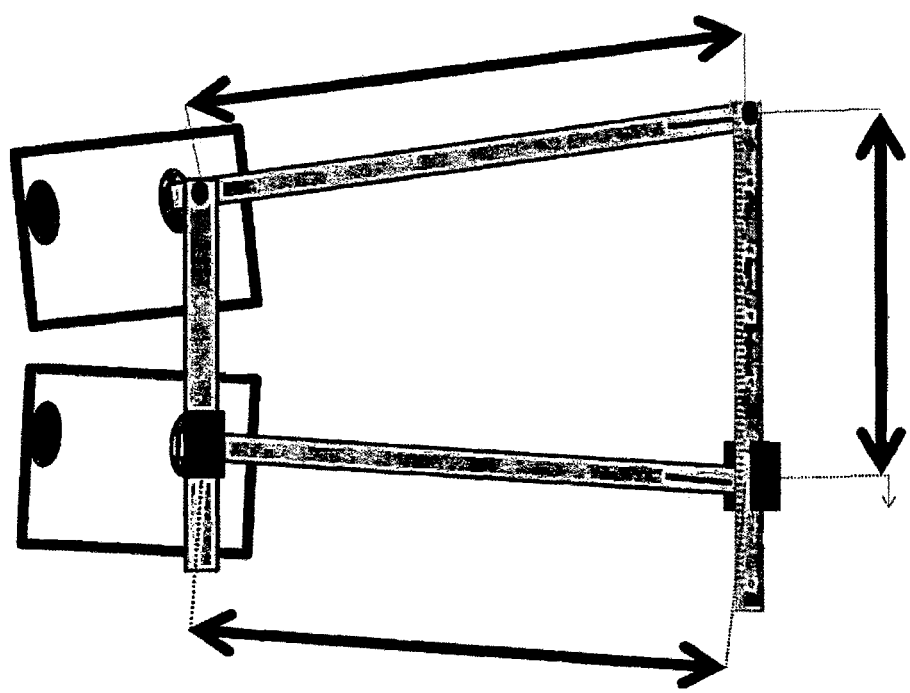

To make this measure (FIG. 42) the center of each pedicle of the convexity is marked and a line is drawn directed to the convexity of height equal to the screw head plus the length of the extender and this is repeated at each level to merge. The total size of the spacers 24 is the sum of all distances in the end between two adjoining spacers less the width of all the separators located in the center subtracting one. Appropriate size spacers will be placed at each level and compensating with other levels.

These measures can also be implemented with the aid of a computer graphic program.

Figure 41:
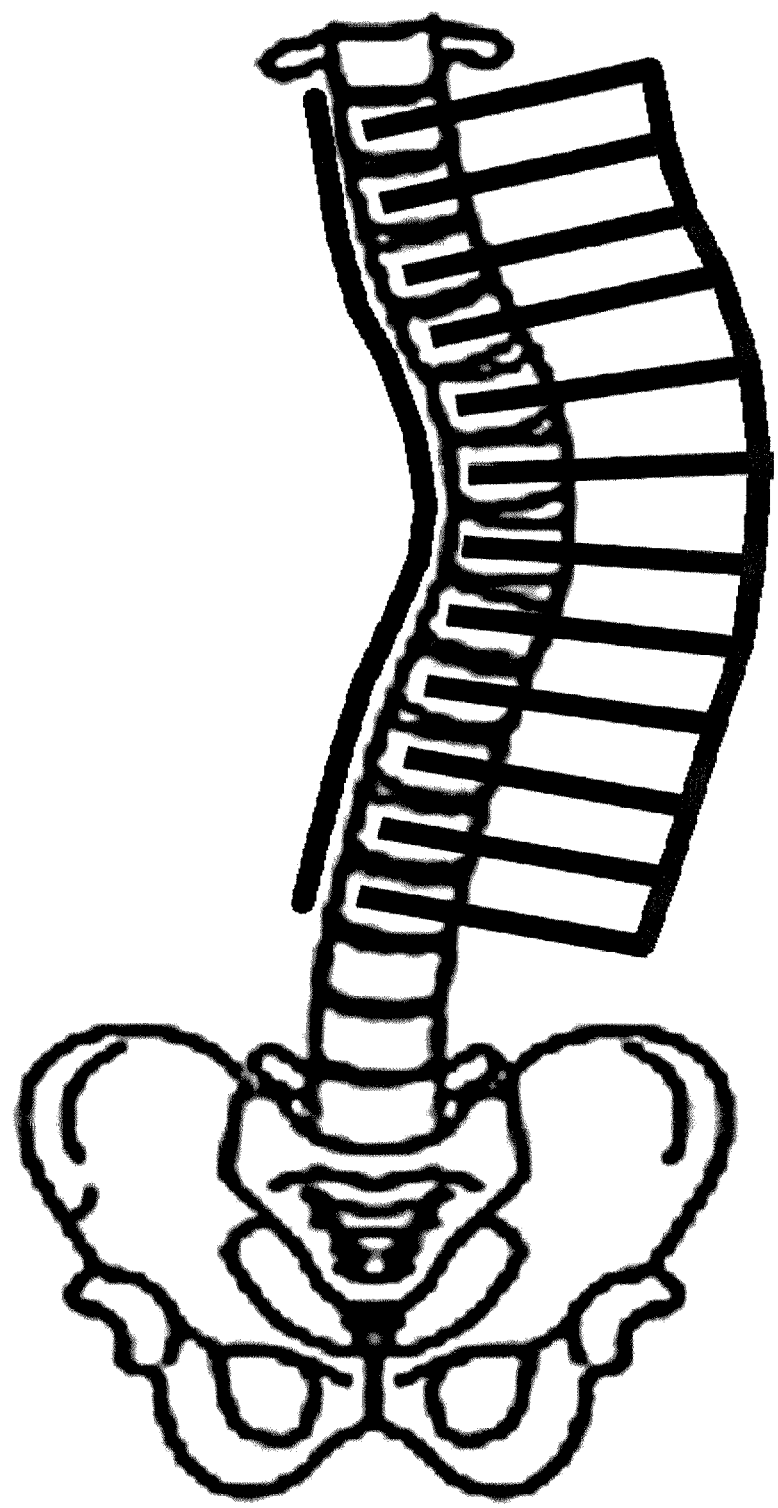
FIGS. 41 and 42 show some preparative pre-operation procedures, to measure the necessary corrections during the operation.

In FIG. 41 an alternative method is exposed:

The inner and external thick lines have the same circumference center but different radii. The radius of the inner line is r, which is calculated from the deflection. The external line is R, equal to the height of r+extension+screw head. The distance (segment of the circumference minus the sum of the diameter of all tubes) is divided by the number of disc spaces and thus the sum of the distance of the spacers can be obtained. Care must be taken to put major extenders in the middle and lower towards the ends, making sure that the total of the ends provide the external line.

This has other significance. The angle of the corrective rod, the bent, must come in a form (or be preformed) so that the calculation of the angle and of the deflection will also provide a value for the spacers 24.

Figure 43A:
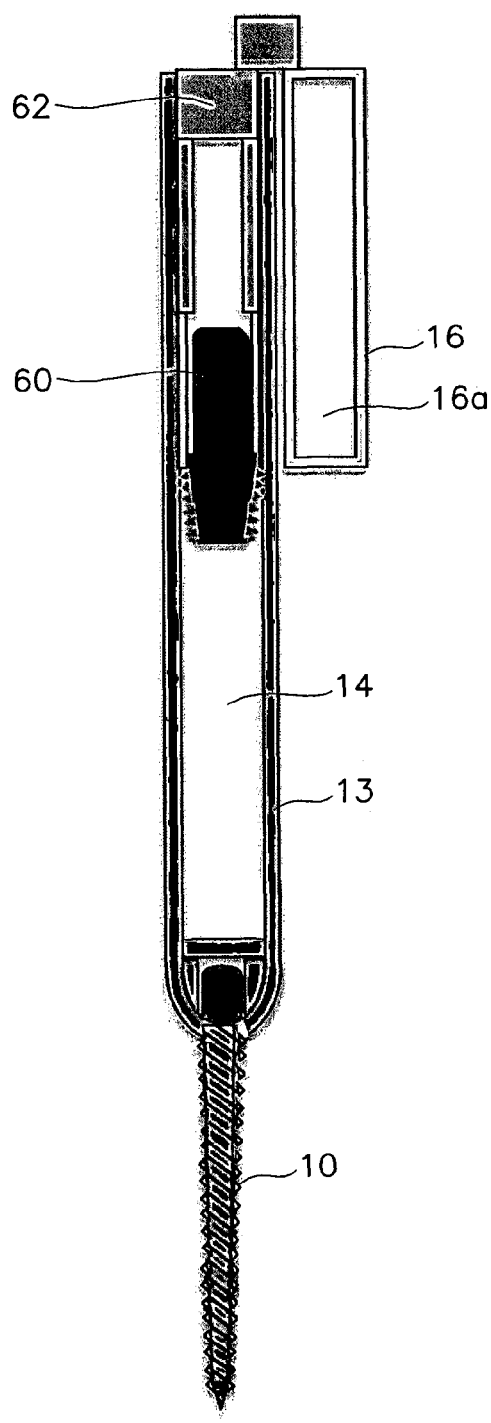
FIGS. 43a and 43b show an embodiment where the extenders used for correction of the convexity are obtained by an extension of the flanges facing each other that define housing between them for implant of first corrective rod.
Figure 43B:
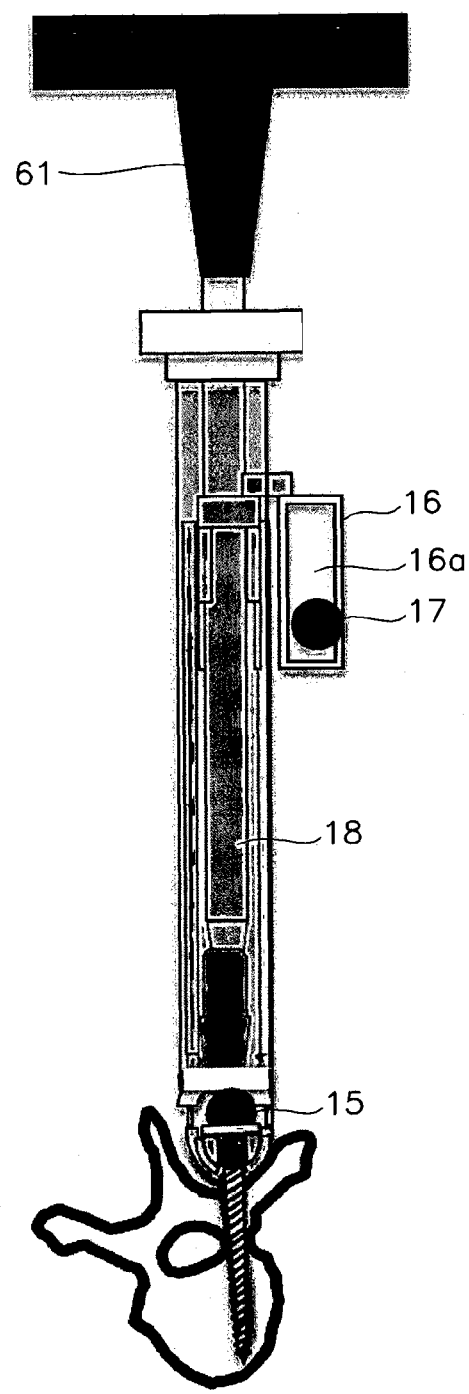

FIGS. 43*a* and 43*b* illustrate another embodiment for the extenders 13, with longitudinal slot 14 allowing insertion of first corrective rod (see FIG. 43*b*), and including retaining member 16 with a passage 16*a* for insertion therethrough of centering rod 17. In this case extenders are directly connected to head 10*a*, i.e. the flanges 12, 12*a* extend longitudinally and form extender 13. An inner core 62 and a rod plug 60 have been provided to allow for preserving tubular condition of extender 13. The core is manually placed inside the extender with a rod plug loaded between the extended flanges delimiting extender 13. The inner core 62 is removable and it is inserted with the rod plug 60 in it, helping to give consistency to the tubular construction and once the rod is sited into the screw head the rod plug 60 is displaced with the screwdriver 61 to lock the rod plug 60 into the head of the screw and in this way attach the reduction rod to the screw.

Figure 45:
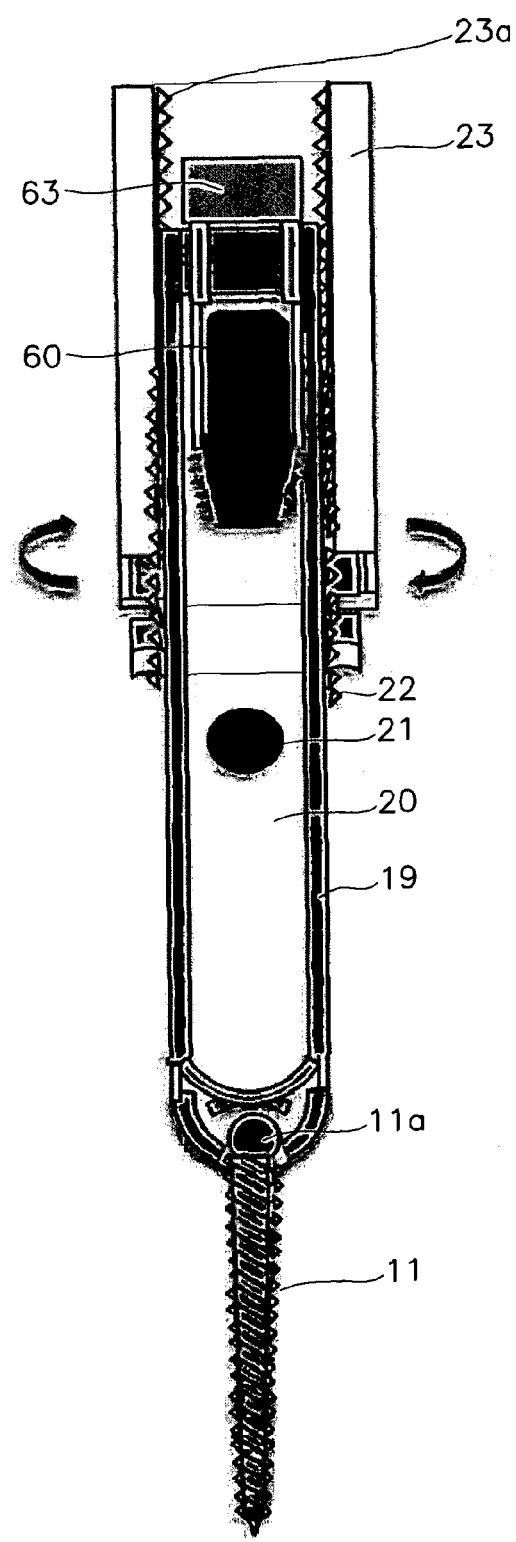
FIG. 45 illustrates and extender used for correction of the concavity with indication of second corrective rod and means to push it towards the implant position.

FIGS. 44*a*, 44*b* and 45 shows an extender 19, constructed as in the case of extender 13 of the previous detailed alternative embodiment by extension of flanges 50*a*, 50*b* (see FIG. 10) providing facing elements between which there are disposed rod plug 60, and connected at the end with inner core 63.

What is claimed is:

1. A system for a global three-dimensional correction of the curvatures of the spine, comprising for each of a plurality of vertebrae of a section of the spine to be corrected:
    a first bone anchoring element configured to be anchored into a vertebra; and
    a second bone anchoring element configured to be anchored into said same vertebra, wherein:
        each bone anchoring element comprises an axial part for insertion into the vertebra and a head;
        said head of said first and second bone anchoring elements comprise pivotally connected thereto a first receiving part and a second receiving part, respectively to which a first alignment elongate member and a second alignment elongate member extending along respective longitudinal axis is are temporally attached by a proximal portion thereof, respectively, each receiving part defines a housing;
        said first alignment elongated member attached to said first bone anchoring element comprises a first longitudinal transversal slot allowing insertion there through, for each of first elongated members in the plurality of vertebrae of a section of the spine to be corrected, of a first corrective rod, said first longitudinal slot connects with said housing and allows said first corrective rod to be displaced from the uppermost part of the first transversal slot to the bottom until reaching said housing of said receiving part to become there implanted and reduce the spinal deformity;
        said second alignment elongated member attached to said second bone anchoring element comprises a second longitudinal transversal slot allowing insertion there through, for each of second elongated members in the plurality of vertebrae of a section of the spine to be corrected, of a second corrective rod, said second longitudinal slot connects with said housing and allows said second corrective rod to be displaced from the uppermost part of the second transversal slot to the bottom until reaching said housing of said receiving part to become there implanted and reduce the spinal deformity;

said first receiving part connected to said head of said first bone anchoring elements is pivotable only in a single sagittal plane to allow for a correction of the convexity of the spine, occurring mainly in a transversal plane, by vertebral translation, by means of the arrangement of said first corrective rod in said housing of the first receiving part;

said second receiving part connected to said head of said second bone anchoring element is pivotable only in a transverse plane perpendicular to said sagittal plane, to allow for a correction of the concavity of the deformed spine occurring mainly in a sagittal plane as the second bone anchoring element follows said second corrective rod, and each elongate member is removed once respective corrective rods are implanted, thereby a change in the vertebral rotation occurs and produces a correction of the axial vertebral deformity and a tridimensional correction of the spine deformity.

2. The system of claim 1 wherein said first and second corrective rods are manufactured with a curvature necessary to correct the spine, on the basis of pre-operative tests conducted on radiographies of a patient based on a method where rods are contoured according to a desired correction.

3. The system of claim 1, wherein said each receiving part comprises a pair of extending elongated flanges facing each other and defining said housing between them wherein said pair of elongated flanges is coupled to respective alignment elongate members and further including between said elongated flanges an inner core and a rod plug.

4. A method for a global three-dimensional correction of the curvatures of the spine, for each of a plurality of vertebrae of a section of the spine to be corrected comprising:

anchoring to a vertebra of a spine section to be corrected a first and a second bone anchoring elements, each having an axial part for insertion into the vertebra and a head provided with a receiving part pivotally connected, said receiving part providing a housing;

attaching to said receiving part of said first anchoring member a first alignment elongated member comprising a first longitudinal transversal slot connecting with said housing;

inserting a first corrective rod trough said first longitudinal transversal slot, for each of first elongated members in the plurality of vertebrae of a section of the spine to be corrected and displacing said first corrective rod from the uppermost part of the first transversal slot to the bottom until reaching said housing of said receiving part of the first anchoring member to become there implanted and reduce the spinal deformity;

attaching to said receiving part of said second anchoring member an second alignment elongated member comprising a second longitudinal transversal slot connecting with said housing;

inserting a second corrective rod trough said second longitudinal transversal slot, for each of first elongated members in the plurality of vertebrae of a section of the spine to be corrected and displacing said second corrective rod from the uppermost part of the second transversal slot to the bottom until reaching said housing of said receiving part of the second anchoring member to become there implanted and reduce the spinal deformity, and removing each elongate member once respective corrective rods are implanted;

wherein said receiving part connected to said head of said first bone anchoring elements is pivotable in a single sagittal plane allowing for a correction mainly in a transversal plane of the convexity of the spine by means of the arrangement of said first corrective rod in said housing and wherein said receiving part connected to said head of said second bone anchoring element is pivotable in a single transverse plane perpendicular to said sagittal plane, allowing for a correction of the concavity of the internal part of the deformed spine mainly in a sagittal plane as the second bone anchoring element follows said second corrective rod, so that the correction in the transverse and sagittal plane is added to the correction of the spinal rotation deformity.

5. The method of claim 4 wherein said displacement of said second corrective rod until being fixed to said housing of the receiving part adjacent said second anchoring element is performed while said first corrective rod is placed in said housing of said receiving part adjacent said first anchoring element but yet not attached thereto.

* * * * *

UNITED STATES PATENT AND TRADEMARK OFFICE
CERTIFICATE OF CORRECTION

PATENT NO. : 9,622,785 B2
APPLICATION NO. : 14/426102
DATED : April 18, 2017
INVENTOR(S) : Ignacio Sanpera Trigueros et al.

It is certified that error appears in the above-identified patent and that said Letters Patent is hereby corrected as shown below:

In the Claims

Column 16, Line 43: "is are," should read "are"

Signed and Sealed this
Twenty-first Day of November, 2017

Joseph Matal
*Performing the Functions and Duties of the
Under Secretary of Commerce for Intellectual Property and
Director of the United States Patent and Trademark Office*